US008658351B2

(12) United States Patent (10) Patent No.: US 8,658,351 B2
Milburn et al. (45) Date of Patent: Feb. 25, 2014

(54) DETERMINING LIVER TOXICITY OF AN AGENT USING METABOLITE BIOMARKERS

(75) Inventors: Michael Milburn, Cary, NC (US); Lining Guo, Chapel Hill, NC (US); Jacob Edward Wulff, Morrisville, NC (US); Kay A. Lawton, Raleigh, NC (US)

(73) Assignee: Metabolon, Inc., Durham, NC (US)

( * ) Notice: Subject to any disclaimer, the term of this patent is extended or adjusted under 35 U.S.C. 154(b) by 0 days.

(21) Appl. No.: 13/148,082

(22) PCT Filed: Feb. 5, 2010

(86) PCT No.: PCT/US2010/023372
§ 371 (c)(1),
(2), (4) Date: Aug. 29, 2011

(87) PCT Pub. No.: WO2010/091290
PCT Pub. Date: Aug. 12, 2010

(65) Prior Publication Data
US 2011/0300571 A1 Dec. 8, 2011

Related U.S. Application Data

(60) Provisional application No. 61/150,535, filed on Feb. 6, 2009.

(51) Int. Cl.
*C12Q 1/00* (2006.01)
(52) U.S. Cl.
USPC .................................................. 435/4
(58) Field of Classification Search
None
See application file for complete search history.

(56) References Cited

U.S. PATENT DOCUMENTS

| 7,452,678 | B2 * | 11/2008 | Durham et al. ........... 435/7.1 |
| 2004/0265889 | A1 | 12/2004 | Durham et al. | |
| 2006/0160237 | A1 | 7/2006 | Du | |

FOREIGN PATENT DOCUMENTS

| JP | 2007295929 | 11/2007 |
| WO | WO 2007/136674 | 11/2007 |
| WO | WO 2008/116867 | 10/2008 |

OTHER PUBLICATIONS

Bass, "Drug-Induced Liver Disease," Current Diagnosis and Treatment in Gastroenterology, $2^{nd}$ ed., Edited by Friedman et al., Lange Medical Books/McGraw-Hill, (2003), pp. 664-679.
Sherlock et al., "Diseases of the Liver and Biliary System," $9^{th}$ ed., Blackwell Scientific Publications, (1993), pp. 17-32.
Batt et al., "Manifestations of Chemically Induced Liver Damage," Clin. Chem., vol. 41, No. 12, (1995), pp. 1882-1887.
De Paiva et al., "Increased Serum Bile Acids as a Possible Biomarker of Hepatotoxicity in Brazilian Workers Exposed to Solvents in Car Repainting Shops," Biomarkers, vol. 10, No. 6, (Nov.-Dec. 2005), pp. 456-463.
International Search Report, issued in PCT/US2010/023372, dated Mar. 31, 2010.
International Preliminary Report on Patentability, issued in PCT/US2010/023372, dated Aug. 18, 2011.
Neghab et al., "Raised Concentration of Serum Bile Acids Following Occupational Exposure to Halogenated Solvents, 1,1,2-trichloro-1,2-2-trifluoroethane and Trichloroethylene," Int Arch Occup Environ Health, vol. 70, (1997), pp. 187-194.
Neghab, M., et al., "Raised Concentration of Serum Bile Acids Following Occupational Exposure to Halogenated Solvents, 1,1,2-trichloro-1,2,2,2-trifluoroethane and Trichloroethylene", *Int. Arch Occup Environ Health*, (1997) vol. 70, pp. 187-194.

* cited by examiner

*Primary Examiner* — Ralph Gitomer
(74) *Attorney, Agent, or Firm* — Brinks Gilson & Lione

(57) ABSTRACT

The present invention provides various biomarkers for hepatotoxicity and various methods of using the biomarkers Some of the biomarkers within the scope of this invention are cholate, glycochenodeoxycholate, glycocholate, taurine, 3-hyroxy-2-ethylpropionate, 4-imidazoleacetate, tyramine, anthranilate, 2'-deoxycytidine, N-acetyl aspartate (NAA), beta-hydroxy-hexanoate, and sarcosine (N-methylglycine) The methods of using the biomarkers include exposing a first hepatocyte culture to a test agent and comparing the levels of the one or more biomarkers obtained in the first hepatocyte culture to the levels of the one or more biomarkers obtained in a second hepatocyte culture without the test agent, where differential levels of the one or more biomarkers in the first hepatocyte culture as compared to the levels in the second hepatocyte culture is indicative of the test agent being a hepatotoxicant.

15 Claims, No Drawings

DETERMINING LIVER TOXICITY OF AN AGENT USING METABOLITE BIOMARKERS

CROSS-REFERENCE TO RELATED APPLICATIONS

This application is a National Stage application of International Application No. PCT/US2010/023372, filed Feb. 5, 2010, which claims the benefit of U.S. Provisional Application No. 61/150,535, filed Feb. 6, 2009, the entire contents of which are hereby incorporated by reference herein.

FIELD

The invention relates generally to methods of identifying and utilizing biomarkers of liver toxicity in a subject.

BACKGROUND

Hepatic toxicity resulting from exposure to an agent needs to be predictable early and easily following exposure to the agent. The liver plays a central role in the metabolism of chemical agents that are taken into the body and as such is susceptible to toxic side effects of the agent and/or its metabolites. This factor is a critical consideration for drug discovery and development activities. It has been reported that over 900 drugs have been implicated in causing liver damage, Friedman, Scott E.; Grendell, James H.; McQuaid, Kenneth R. (2003). *Current diagnosis & treatment in gastroenterology*. New York: Lang Medical Books/McGraw-Hill. pp. p664-679. Pharmaceutical companies extensively test new chemical entities for toxic effects on the liver throughout the development process, from pre-clinical through clinical stages, yet drugs continue to be taken off the market due to late discovery of hepatotoxicity.

The available tests for liver function can be divided into dynamic tests and essential and special static tests. Dynamic tests reflect real-time hepatic function in which the dimension of time is also considered, in which clearance of a test substance or the formation rate of a biochemical reflects the actual performance of the liver. Due to difficulty of use, many dynamic tests have not found widespread clinical or laboratory application.

Traditional static tests, while simpler, are only an indirect measure of hepatic function or damage and involve the measurement of a biomarker at a single point in time. Essential static tests for compromised liver function include aspartate aminotransferase (AST), alanine aminotransferase (ALT) (for hepatocellular damage), glutamate dehydrogenase (GLDH), alkaline phosphatase (AP) (for cholestasis, hepatic infiltrations), γ-glutamyltransferase (γ-GT) (for cholestatis, alcohol abuse), bilirubin (conjugation, excretory function, to assess severity), cholinesterase, albumin, and γ-globulin (for chronic hepatitis, cirrhosis, following the course of chronic disease).

There are several limitations associated with these conventional liver function tests. For example, test results of liver enzymes and clotting factors can be affected by the substitution of blood components. Falling aminotransferase values are only reassuring when accompanied by a restoration of metabolic function. Aminotransferases, alkaline phosphatase and bilirubin lack organ specificity. The long plasma half-life of cholinesterase does not allow the detection of rapid changes in hepatic function. Most importantly, the conventional tests are only of limited prognostic value.

More specialist static tests include bile acids indicating excretory function and portosystemic shunting, ammonia as a marker of reduced urea synthesis, and parameters reflecting fibrotic activity such as aminoterminal procollagen type III peptide and other well-known tests. Sherlock et al., *Assessment of liver function in Diseases of the Liver and Biliary System*, 9th ed., Oxford: Blackwell Scientific Publications, pp. 17-32, 353 (1993). Further diagnostic criteria include the immunoglobulins, indicating humoral immunoresponse and autoantibodies for the assessment of autoimmune liver diseases and viral hepatitis markers. Serum hyaluronic acid has been proposed as a noninvasive index of the severity of cirrhosis in chronic viral hepatitis and as a measure of response to antiviral therapy. In alcoholic liver disease, serum hyaluronic acid can be applied for the assessment of hemodynamic changes. Serum alpha-glutathione S-transferase (GST) is an emerging static test indicating hepatocellular damage with application in transplant rejection. However, these tests are not useful for in vitro assays using hepatocytes or other cell or organ cultures.

SUMMARY

In one embodiment, a method of determining whether an agent is a hepatotoxicant is provided. The method comprises (a) incubating a first hepatocyte culture in the presence of a test agent; (b) incubating a second hepatocyte culture in the absence of the test agent; (c) measuring the level(s) of one or more biomarker(s) selected from the group of biomarkers listed in Table(s) 1, 2, and 18 in the first and second hepatocyte cultures; and (d) comparing the level(s) of the one or more biomarker(s) obtained in the first hepatocyte culture to the level(s) of the one or more biomarkers obtained in the second hepatocyte culture, wherein differential level(s) of the one or more biomarker(s) in the first hepatocyte culture as compared to the level(s) in the second hepatocyte culture is indicative of the test agent being a hepatotoxicant.

In a further embodiment, a method of determining whether an agent is a hepatotoxicant, is provided, comprising: administering a test agent to a subject; measuring the level(s) of one or more biomarkers selected from the biomarkers listed in Tables 1, 2, 6, 7, 8, 9, 10, 11, 12, 13, 14, 15, 16, 17, and 18 in a biological sample obtained from the subject; and comparing the level(s) of the one or more biomarkers in the sample(s) to hepatoxicity-positive and/or hepatoxicity-negative reference levels of the one or more biomarkers in order to determine whether the test agent is hepatotoxicant.

DETAILED DESCRIPTION

The present invention related to biomarkers of liver toxicity. Methods, systems, and compositions for detecting liver toxicity in response to an agent in a subject are provided. Methods and systems for identifying and utilizing one or more (e.g. multi-analyte) biomarkers for predicting the effect of an agent on liver function (i.e., hepatotoxicity) in a subject are also provided. Prior to describing this invention in further detail, however, the following terms will first be defined.

Definitions

A "reference level" of a biomarker means a level of the biomarker that is indicative of a particular disease state, phenotype, or lack thereof, as well as combinations of disease states, phenotypes, or lack thereof. A "positive" reference level of a biomarker means a level that is indicative of a particular disease state or phenotype. A "negative" reference level of a biomarker means a level that is "hepatotoxicity-positive reference level" of a biomarker means a level of a biomarker that is indicative of a positive diagnosis of liver toxicity in a subject, and a "hepatotoxicity-negative reference level" of a biomarker means a level of a biomarker that is indicative of a negative diagnosis of liver toxicity in a subject. A "reference level" of a biomarker may be an absolute or relative amount or concentration of the biomarker, a presence or absence of the biomarker, a range of amount or concentration of the biomarker, a minimum and/or maximum amount or concentration of the biomarker, a mean amount or concentration of the biomarker, and/or a median amount or concentration of the biomarker; and, in addition, "reference levels" of combinations of biomarkers may also be ratios of absolute or relative amounts or concentrations of two or more biomarkers with respect to each other. Appropriate positive and negative reference levels of biomarkers for a particular disease state, phenotype, or lack thereof may be determined by measuring levels of desired biomarkers in one or more appropriate subjects or cell lines, and such reference levels may be tailored to specific populations of subjects (e.g., a reference level may be age-matched so that comparisons may be made between biomarker levels in samples from subjects of a certain age and reference levels for a particular disease state, phenotype, or lack thereof in a certain age group). Such reference levels may also be tailored to specific techniques that are used to measure levels of biomarkers in biological samples (e.g., LC-MS, GC-MS, etc.), where the levels of biomarkers may differ based on the specific technique that is used.

The "level" of one or more biomarkers means the absolute or relative amount or concentration of the biomarker in the sample.

"Sample" or "biological sample" means biological material isolated from a subject. The biological sample may contain any biological material suitable for detecting the desired biomarkers, and may comprise cellular and/or non-cellular material from the subject. The sample can be isolated from any suitable biological tissue or fluid such as, for example, blood, blood plasma, serum, urine, or liver tissue.

The biomarkers described herein were discovered using metabolomic profiling techniques. Such metabolomic profiling techniques are described in more detail in the Examples set forth below as well as in U.S. Pat. Nos. 7,005,255; 7,329,489; 7,550,258; 7,550,260; 7,553,616; 7,635,556 and U.S. patent application Ser. No. 11/301,077 (Publication No. 2006/0134676), Ser. No. 11/301,078 (Publication No. 2006/0134677), and Ser. No. 11/301,079 (Publication No. 2006/0134678), the entire contents of which are hereby incorporated herein by reference.

Generally, metabolic profiles were determined for biological samples from subjects having liver toxicity as compared to other subjects not having liver toxicity.

The biomarkers are discussed in more detail herein. The biomarkers that were discovered correspond with the following groups:

1. Biomarkers in Urine that are indicative of Liver Toxicity (listed in Table 6);
2. Biomarkers in Urine that are indicative of Necrosis (listed in Table 7);
3. Biomarkers in Urine that are indicative of Cholestasis and/or Steatosis (listed in Table 8);
4. Biomarkers in Urine that are indicative of liver toxicity in humans but for which there is no associated histopathology or clinical chemistry change in rats (listed in Table 9);
5. Biomarkers in plasma that are indicative of Liver Toxicity (listed in Table 10);
6. Biomarkers in Plasma that are indicative of Necrosis (listed in Table 11);
7. Biomarkers in Plasma that are indicative of Cholestasis and/or Steatosis (listed in Table 12);
8. Biomarkers in Plasma that are indicative of liver toxicity in humans but for which there is no associated histopathology or clinical chemistry change in rats (listed in Table 13);
9. Biomarkers in liver tissue that are indicative of liver toxicity (listed in Table 14);
10. Biomarkers in liver tissue that are indicative of necrosis (listed in Table 15);
11. Biomarkers in liver tissue that are indicative of Cholestasis and/or Steatosis (listed in Table 16);
12. Biomarkers in liver tissue that are indicative of liver toxicity in humans but for which there is no associated histopathology or clinical chemistry change in rats (listed in Table 17); and
13. Combined Biomarkers that are indicative of liver toxicity (Table 18).

Although the identities of some of the biomarkers and non-biomarker compounds are not known at this time, such identities are not necessary for the identification of the biomarkers or non-biomarker compounds in biological samples from subjects, as the "unnamed" compounds have been sufficiently characterized by analytical techniques to allow such identification. The analytical characterization of all such "unnamed" compounds is listed in the Examples. Such "unnamed" biomarkers and non-biomarker compounds are designated herein using the nomenclature "Metabolite" followed by a specific metabolite number.

In some embodiments, methods are provided for determining whether an agent is a hepatotoxicant, comprising: administering a test agent to a subject; measuring the level(s) of one or more biomarkers selected from the biomarkers listed in Tables 6, 10, 14, and 18 in a biological sample obtained from the subject; and comparing the level(s) of the one or more biomarkers in the sample(s) to hepatotoxicity-positive and/or hepatotoxicity-negative reference levels of the one or more biomarkers in order to determine whether the test agent is a hepatotoxicant. Sample-type specific (e.g., urine, plasma, and liver tissue) biomarkers are provided (e.g., Tables 6 (urine), 10 (plasma), and 14 (liver tissue)), as are biomarkers for specific liver damage for each type of sample (i.e., Tables 7 (biomarkers in urine indicative of necrosis); 8 (biomarkers in urine indicative of cholestasis and/or steatosis); 11 (biomarkers in plasma indicative of necrosis), 12 (biomarkers in plasma indicative of cholestasis and/or steatosis); 15 (biomarkers in liver tissue indicative of necrosis); and 16 (biomarkers in liver tissue indicative of cholestasis and/or steatosis). In some instances, the biomarkers used in a method may comprise 3-hyroxy-2-ethylpropionate, 4-imidazoleacetate, tyramine, anthranilate, 2'-deoxycytidine, N-acetylaspartate (NAA), beta-hydroxyhexanoate, and sarcosine (N-methylglycine).

Biomarkers were discovered that are indicative of liver toxicity in humans but for which there is no associated histopathology or clinical chemistry change in rats. These biomarkers were also sample-specific (e.g., Table 9, 13, and 17). Such biomarkers are valuable to estimate the chemical's potential to cause human specific hepatotoxicity.

After the level(s) of the one or more biomarkers in the sample are determined, the level(s) are compared to hepatotoxicity-positive and/or hepatotoxicity-negative reference levels to aid in determining or to determine whether the test agent is hepatotoxicant. Levels of the one or more biomarkers in a sample corresponding to the hepatotoxicity-positive reference levels (e.g., levels that are the same as the reference levels, substantially the same as the reference levels, above and/or below the minimum and/or maximum of the reference levels, and/or within the range of the reference levels) are indicative of the test agent being a hepatotoxicant. Levels of the one or more biomarkers in a sample corresponding to the hepatoxicity-negative reference levels (e.g., levels that are the same as the reference levels, substantially the same as the reference levels, above and/or below the minimum and/or maximum of the reference levels, and/or within the range of the reference levels) are indicative of the test agent not being a hepatotoxicant. In addition, levels of the one or more biomarkers that are differentially present (especially at a level that is statistically significant) in the sample as compared to hepatoxicity-negative reference levels are indicative of the test agent being a hepatotoxicant. Levels of the one or more biomarkers that are differentially present (especially at a level that is statistically significant) in the sample as compared to hepatoxicity-positive reference levels are indicative of the test agent not being a hepatotoxicant.

Any suitable method may be used to detect the biomarkers in a biological sample in order to determine the level(s) of the one or more biomarkers. Suitable methods include chromatography (e.g., HPLC, gas chromatography, liquid chromatography), mass spectrometry (e.g., MS, MS-MS), enzyme-linked immunosorbent assay (ELISA), antibody linkage, other immunochemical techniques, and combinations thereof (e.g. LC-MS-MS). Further, the level(s) of the one or more biomarkers may be detected indirectly, for example, by using an assay that measures the level of a compound (or compounds) that correlates with the level of the biomarker(s) that are desired to be measured.

In some embodiments, the biological samples for use in the detection of the biomarkers are transformed into analytical samples prior to the analysis of the level or detection of the biomarker in the sample. For example, in some embodiments, protein extractions may be performed to transformed the sample prior to analysis by, for example, liquid chromatography (LC) or tandem mass spectrometry (MS-MS), or combinations thereof. In other embodiments, the samples may be transformed during the analysis, for example by tandem mass spectrometry methods.

Any number of biomarkers may be used in the methods disclosed herein. That is, the disclosed methods may include the determination of the level(s) of one biomarker, two or more biomarkers, three or more biomarkers, four or more biomarkers, five or more biomarkers, six or more biomarkers, seven or more biomarkers, eight or more biomarkers, nine or more biomarkers, ten or more biomarkers, fifteen or more biomarkers, etc., including a combination of all of the biomarkers in Table 4 and/or Table 4B. In another aspect, the number of biomarkers for use in the disclosed methods include the levels of about twenty-five or less biomarkers, twenty or less, fifteen or less, ten or less, nine or less, eight or less, seven or less, six or less, five or less biomarkers. In another aspect, the number of biomarkers for use in the disclosed methods include the levels of one, two, three, four, five, six, seven, eight, nine, ten, eleven, twelve, thirteen, fourteen, fifteen, twenty, or twenty-five biomarkers.

In one embodiment, single-analyte or multi-analyte diagnostic biomarkers of clinical end-points for use in the methods of the present invention can be identified from large-scale molecular assays of non-invasively obtained biological samples including urine, serum, or blood. In some cases, the response of numerous analytes is reflective of a change in physiology indicative of efficacy, toxicity, disease, or physiological change, and the comprehensive nature of the data set enables an in toto evaluation of general response. Robertson (2005) *Toxicological Sciences* 85:809-822. A variety of spectroscopic methods can be used to generate comprehensive data sets from large-scale molecular assays on complex biological samples, including Mass Spectrometry (MS) and Nuclear Magnetic Resonance (NMR). See Lindon et al. (2004) *Biomarkers* 9:1-31. The MS and NMR approaches are complementary, giving information on different sets of biomarkers. However, there are few reported metabonomic studies on mammalian systems in the literature that have used MS as an experimental approach and even fewer that have identified novel biomarkers. See Lindon et al. Furthermore, actually generating such biomarkers presents numerous analytical, computational and biological challenges. Accordingly, there remains a need for the identification of general single or multi-analyte hepatotoxicity biomarkers useful for predicting in vivo hepatic toxicity of an agent.

One or more of the biomarkers described herein may be used to predict toxicity of an agent in vitro or gauge toxic effects of an agent in vivo. A single set of biomarkers using reagents and standards could be used, for example, to evaluate therapeutic candidate compounds from initial screening, through testing in pre-clinical species, and potentially in clinical trials. Further, such analytes could be useful to predict toxicity of other chemical agents such as agrochemicals or environmental agents (e.g., xenobiotics, mycotoxins). Such universal indicators of toxicity may provide one or more advantages. For example, they may correctly identify toxic compounds with diverse mechanisms of action, including various chemical classes. In addition, changes in these biomarkers may be consistent, quantifiable and reflect the degree, type, or course of toxic insult. Also, assays may be adaptable to high throughput technologies without becoming prohibitively expensive. Further, in vivo sample collection may be non- or minimally invasive, e.g. urine or blood. The disclosure provides a system and method of using hepatotoxicity biomarkers to predict the incidence of hepatotoxicity for a particular compound both in vitro as well as in vivo that may provide one or more of these advantages.

Thus, the present invention encompasses a method of predicting hepatotoxicity of a test substance comprising the steps of: a) incubating a hepatocyte in the presence and absence of a test substance; and b) comparing levels of at least one biomarker selected from the group consisting of the biomarkers listed in Table(s) 1 and/or 2 (i.e., Liver Toxicity panel) or Tables 6, 7, 8, 9, 10, 11, 12, 13, 14, 15, 16, 17, and/or 18, in the presence and absence of said test substance; wherein a level of the biomarker(s) in the presence of the test substance indicates that the test substance is predicted to cause hepatotoxicity. The levels of the biomarker(s) can be measured using any method available for measuring biomarker(s), including, for example, high performance liquid chromatography coupled to tandem mass spectrometry to determine the relative abundance of said biomarker(s) in the presence and absence of said test substance.

In some embodiments, the levels of the one or more biomarker(s) listed in Table(s) 1 and/or 2 or Tables 6, 7, 8, 9, 10, 11, 12, 13, 14, 15, 16, 17, and/or 18 can be compared to reference levels of the biomarker(s), for use in predicting the hepatoxicity of a test substance.

In other embodiments, the levels of the one or more biomarker(s) listed in Table(s) 1 and/or 2 or Tables 6, 7, 8, 9, 10, 11, 12, 13, 14, 15, 16, 17, and/or 18 produced by cells cultured in the presence of a test substance can be compared to levels of the respective biomarker(s) produced by cells cultured in the absence of the test substance ("control" level(s)). Such comparisons may be used to detect differential levels (e.g., increases or decreases) of the one or more biomarker(s) from exposure to a test substance. Any number of biomarkers may be used in the methods disclosed herein. That is, the disclosed methods may include the determination of the level(s) of one biomarker, two or more biomarkers, three or more biomarkers, four or more biomarkers, five or more biomarkers, six or more biomarkers, seven or more biomarkers, eight or more biomarkers, nine or more biomarkers, ten or more biomarkers, fifteen or more biomarkers, etc., including a combination of all of the biomarkers in Table(s) 1 and/or 2 or Tables 6, 7, 8, 9, 10, 11, 12, 13, 14, 15, 16, 17, and/or 18. In another aspect, the number of biomarkers for use in the disclosed methods include the levels of about thirty or less biomarkers, twenty-five or less, twenty or less, fifteen or less, ten or less, nine or less, eight or less, seven or less, six or less, five or less biomarkers. In another aspect, the number of biomarkers for use in the disclosed methods include the levels of one, two, three, four, five, six, seven, eight, nine, ten, eleven, twelve, thirteen, fourteen, fifteen, twenty, twenty-five, or thirty biomarkers.

In one embodiment, a method of detecting liver toxicity in a subject is provided comprising the following steps: a) administering a test substance to a subject (e.g., animal, mammal, rat, mouse, dog, rabbit, non-human primate, human); and b) comparing levels of at least one biomarker selected from the group consisting of the biomarkers listed in Table(s) 1 and/or 2 (i.e., Liver Toxicity panel), in a sample from the subject before administration of said test substance and at one or more time-points after administration of said test substance; wherein the level of said biomarker(s) in sample collected after administration of the test substance indicates whether the substance is predicted to cause hepatotoxicity, and wherein the level of said biomarker(s) is measured using, for example, high performance liquid chromatography coupled to tandem mass spectrometry to determine the relative abundance of said biomarker(s) in the presence and absence of said test substance.

In another embodiment, a method of monitoring progression/regression of liver toxicity in a subject is provided, where the method comprises: analyzing a first biological sample from a subject to determine the level(s) of one or more biomarkers for hepatotoxicity in the sample, wherein the one or more biomarkers are selected from Table(s) 1 and/or 2 or Tables 6, 7, 8, 9, 10, 11, 12, 13, 14, 15, 16, 17, and/or 18 and the first sample is obtained from the subject at a first time point; analyzing a second biological sample from a subject to determine the level(s) of the one or more biomarkers, wherein the second sample is obtained from the subject at a second time point; and comparing the level(s) of one or more biomarkers in the first sample to the level(s) of the one or more biomarkers in the second sample in order to monitor the progression/regression of hepatotoxicity in the subject.

In another embodiment a method of detecting liver toxicity in a subject is provided comprising the following steps: a) subjects (e.g., animal, mammal, rat, mouse, dog, rabbit, non-human primate, human) are administered a test substance and a biological sample is obtained at various times after administration of said substance; and b) comparing levels of at least one biomarker selected from the group consisting of the biomarkers listed in Table(s) 1 and/or 2 (i.e., Liver Toxicity panel) or Tables 6, 7, 8, 9, 10, 11, 12, 13, 14, 15, 16, 17, and/or 18, in a sample from the subject to which said test substance was administered to reference level of said biomarker; wherein the level of said biomarker(s) in sample collected after administration of the test substance indicates whether the substance is predicted to cause hepatotoxicity, and wherein the level of said biomarker(s) is measured using, for example, high performance liquid chromatography coupled to tandem mass spectrometry to determine the relative abundance of said biomarker(s) in the presence and absence of said test substance.

In a further embodiment, said biomarker(s) levels are used to generate an index or score that is useful to determine the level of hepatotoxicity of said compound. A sample is obtained from a cell culture exposed to known hepatoxicant(s). The level of each biochemical in a panel (e.g. one or more biomarkers listed in Table(s) 1 and/or 2) is determined for each sample. A classifier is built that correlates the degree of liver toxicity to the levels of biochemicals in the panel for each sample. The levels of each biochemical in the panel of biochemicals is determined for a sample derived from a test cell culture. The classifier is then used to determine the presence of liver toxicity in the test sample. In some embodiments, the sample source may be obtained following in vivo exposure to the agent (e.g. using a model animal system, such as a rat, mouse, rabbit, dog or other mammal) and the sample source may be one or more selected from a group that includes, without limitation, blood, serum, urine, cells, tissue or any combination thereof.

The classifier for use in the methods of the present invention may be correlated to any degree or type of liver toxicity in a cell sample. For example the classifier can be used to classify a marker into a level or degree of toxicity, such as no toxicity, a low level of toxicity, a mid level of toxicity, a high level of toxicity, or a very high level of toxicity. Alternatively, a classifier may be built that correlates the degree of liver toxicity to clinical measures of liver toxicity, such as the CIOMS/RUCAM scale. For example, the CIOMS/RUCAM scale may be used to correlate the level of one or more biomarkers listed in Table(s) 1 and/or 2 to categorize the level on a scale of 1 to 8 or more, where a score of more than 8 refers to a "definite or highly probable" category of toxicity, a score of 6 to 8 refers to a "probable" category of toxicity, a score of 3-5 refers to a "possible" category of toxicity, a score of 1-2 refers to an "unlikely" category of toxicity, and a score of zero refers to an "excluded" from toxicity category.

The classifier for use in the methods of the present invention can also be correlated to the type, stage, or histopathology of liver toxicity, such as necrosis/apoptosis, hepatitis, cholestasis, steatosis, phospholipidosis, granuloma, vascular lesions, neoplasms, and sclerosis.

In some embodiments, the classifier is implemented in a computer program. A computer program with an appropriate application interface may be created and stored on a computer system and/or a program storage device to assist in performing the methods of the present invention.

In some embodiments, the levels of biomarkers listed in Table(s) 1 and/or 2 or Tables 6, 7, 8, 9, 10, 11, 12, 13, 14, 15, 16, 17, and/or 18 may be different depending on the toxicant present. For example, the level of one biomarker may increase in response to toxicity caused by one toxicant, but decrease in response to the toxicity of a different toxicant (or remain unchanged).

In some embodiments, a method of determining liver toxicity in test cells or a subject is provided comprising the following steps. A sample is obtained from cultured cells or a subject who has been, or who is suspected of having been, exposed to a toxic agent. The levels of each biochemical in a panel (e.g. one or more biomarkers listed in Table(s) 1 and/or 2 or Tables 6, 7, 8, 9, 10, 11, 12, 13, 14, 15, 16, 17, and/or 18) of biochemicals is determined for the sample. The levels are input into a classifier associated with the panel. An output is obtained from the classifier, the output being indicative of whether liver toxicity has occurred in the subject. The levels of the biochemicals in the sample can be determined by any method.

The cells for use in any of the methods disclosed herein may be obtained from any source of cells which may be cultured with a toxic substance or a substance suspected of having toxicity to the liver. In one embodiment, the cells are obtained from liver tissue of a mammalian subject, such as a human, rat, guinea pig, mouse, cat, dog, horse, pig, cow, or non-human primate. Such liver cells may be cultured using any culture method available.

The methods disclosed herein can be utilized in conjunction with other known analyte biomarkers, including without limitation one or more of the analytes AST (aspartate aminotransferase), ALT (alanine aminotransferase), GLDH (glutamate dehydrogenase), AP (alkaline phosphatase), γ-GT (γ-glutamyltransferase), bilirubin, cholinesterase, albumin, and γ-globulin, or any combination thereof. As will be evident to one of skill in the art, the classifiers utilized in these methods can be embodied in a computer or other electronic system. Furthermore, kits are provided for carrying out the methods described above.

Table(s) 1 and/or 2 provide(s) a list of biomarkers that change in response to different liver toxicants, and one or more of which may be used in the methods disclosed herein. The listed biomarkers demonstrate different responses to different agents. For example, the levels of some biomarkers increase in response to one particular toxicant, while it decreases in response to a different toxicant. In addition, the level of a toxicant may increase initially, then decrease below the peak level or even below the control level over a period of time, such as 6 hours, 1 day, 2, 3, 4, 5, 6, 7, or more days. Alternatively, the level of a toxicant may decrease initially, then increase above the trough level or even above the control level over a period of time, such as 6 hours, 1 day, 2, 3, 4, 5, 6, 7, or more days.

TABLE 1

Hepatotoxicity Biomarker Panel

|   | Biomarker Compound | Change in Response to Liver Toxicant 1 | Change in Response to Liver Toxicant 2 |
|---|---|---|---|
| 1 | Glycochenodeoxycholate | Increase | Increase |
| 2 | Glycocholate | Increase | Increase |
| 3 | Taurochenodeoxycholate | Increase | |
| 4 | Chenodeoxycholate | Increase | |
| 5 | Deoxycholate | Increase | |
| 6 | Ursodeoxycholate | Increase | Increase |
| 7 | Cholate | Increase | Increase |
| 8 | Glycodeoxycholate | Increase | Increase |
| 9 | Taurocholate | Increase | Decrease |
| 10 | Taurodeoxycholate | Increase | Decrease |
| 11 | Lithocholate | Increase | |
| 12 | beta-muricholate | Increase | Decrease |
| 13 | gamma-glutamyl dipeptides: e.g., Gamma-glutamylalanine, glutamylisoleucine, glutamylleucine, glutamyltaurine, gamma-glutamylglutamate, gamma-glutamylphenylalanine, gamma-gluamyltyrosine, gamma-glutamylthreonine, etc. | Increase | |
| 14 | Pipecolate | Increase | Decrease |
| 15 | 4-hydroxyphenyllactate | Increase | |
| 16 | 4-hydroxyphenylpyruvate | Increase | |
| 17 | Phenylpyruvate | Increase | |
| 18 | Phenylacetate | Increase | |
| 19 | Indole lactate | Increase | Increase then Decrease |

TABLE 1-continued

Hepatotoxicity Biomarker Panel

|   | Biomarker Compound | Change in Response to Liver Toxicant 1 | Change in Response to Liver Toxicant 2 |
|---|---|---|---|
| 20 | Quinolinate | Increase | |
| 21 | Kynurenine | Increase | Decrease |
| 22 | 2-aminoadipate | Increase | |
| 23 | Urocanate | Increase | |
| 24 | Methylthioadenosine | Increase | |
| 25 | Ophthalmate | Increase | |
| 26 | 2-aminobutyrate | Increase | Increase |
| 27 | Glutathione | Increase | Decrease |
| 28 | Allantoin | Increase | Decrease then slight increase |
| 29 | Dimethylarginine, asymetrical (ADMA) | Increase | |
| 30 | Dimethylarginine, symetrical (SDMA) | Increase | |
| 31 | beta-alanine | Increase | |
| 32 | beta-aminoisobutyrate | Increase | |
| 33 | beta-ureidoisobutyrate | Increase | |

TABLE 2

Hepatotoxicity Biomarker Panel:

glycochenodeoxycholate,
glycocholate,
taurochenodeoxycholate,
chenodeoxycholate,
deoxycholate,
ursodeoxycholate,
cholate,
glycodeoxycholate,
taurocholate,
taurodeoxycholate,
litocholate,
beta-muricholate (for RATS!)
Various gamma-glutamyl dipeptides
4-hydroxyphenyllactate
4-hydroxyphenylpyruvate,
phenylacetate,
Indole lactate
quinolinate
kynurenine
2-aminoadipate
urocanate,
methylthioadenosine
glutamyl dipeptides,
ophthalmate
2-aminobutyrate
dimethylarginine (ADMA)
dimethylarginine (SDMA)
beta-alanine
beta-aminoisobutyrate
beta-ureidoisobutyrate Compounds that are widely known to cause hepatic injury in animals and/or in man, as described in "Toxicology of the liver", $2^{nd}$ Ed. By G. L. Plaa and W. R. Hewitt, Target Organ Toxicology Series, 1997 are listed in Table 2. The modulation of biomarker levels by several compounds that show a similar type of hepatotoxicity (e.g., necrosis, steatosis, cholestasis) defines a characteristic profile which is expected to be similar for further compounds that elicit the same type of toxicity. Thus, these biochemical profiles can be used for the prediction of the toxic potential of unknown compounds. The characteristic profiles that are useful to indicate the classes of hepatotoxins are thus defined.

Accordingly, in one embodiment, the present invention relates to a method of predicting at least one toxic effect of a compound, comprising detecting the level of one or more biomarkers from Table(s) 1 and/or 2 of Tables 6, 7, 8, 9, 10, 11, 12, 13, 14, 15, 16, 17, and/or 18 in a tissue, cell or animal sample exposed to the compound, wherein differential abundance relative to a non-toxic reference level or control level of the one or more biomarkers in Table(s) 1 and/or 2 or Tables 6, 7, 8, 9, 10, 11, 12, 13, 14, 15, 16, 17, and/or 18 is indicative of at least one toxic effect.

In one embodiment, the biomarker levels are determined using a dansylation assay, a method for the sensitive determination of amino acids and amines in urine and plasma biological matrices by isotope dilution LC-MS-MS after dansylation.

Dansylation products show generally a significant signal enhancement in reversed phase ESI- and APCI-LC-MS compared to the genuine analyte species. The enhancement is due to increased ionization through introduction of a basic dimethylamino moiety and increased hydrophobicity of the dansylation product. The basic dimethylamino improves protonation of the analyte. The higher hydrophobicity facilitates elution at a higher organic solvent content of the mobile phase under reversed phase conditions. This higher content of volatile organic solvents enhances ionization through faster and better evaporation of the mobile phase in the LC-MS interface.

In an embodiment of this method, samples are spiked with isotopically stable labeled internal standards. If urine is used as a biological matrix it can be derivatized directly with dansyl chloride without further sample pretreatment. Biological samples that contain proteins (e.g., plasma, CSF, cells, tissue) may require a protein precipitation step by mixing with an organic solvent. After removal of the proteins by centrifugation a portion of the deproteinized extract is derivatized with dansyl chloride. An aliquot of the respective reaction mixtures is directly injected without further processing onto a LC-MS-MS system equipped with a reversed phase U-HPLC column. The peak areas of the respective analyte product ions are measured against the peak area of the product ions of the isotopically labeled internal standards. Quantification is performed using a weighted linear least squares regression analysis.

EXAMPLES

Example 1

Identification of Biomarkers for Determining/Predicting the Liver Toxicity of Compounds To determine specific biochemical markers for liver toxicity (as well as biochemical markers for various type of liver toxicity) induced by compositions such as drugs or other chemicals, and to further validate the identified liver toxicity markers of Table(s) 1 and/or 2, the following experiments were carried out.

Rats were treated daily with a single oral dose of a known liver toxicants at low and high doses (as shown in Table 3) as well as with a vehicle control containing none of the toxicant. The hepatotoxic agents listed in Table 3 are known to induce distinct types of liver histopathology as described in Table 4.

Plasma, urine, and liver samples were collected at day 2 and day 5 for metabolomic analysis, liver histopathology, and routine clinical chemistry (i.e., aspartate aminotransferase (AST), alanine aminotransferase (ALT), total bilirubin (TBIL), alkaline phosphatase (ALP)).

TABLE 3

Liver Toxicants and Dosages

| Drug | Dose (mg/kg) |
|---|---|
| Acetaminophen | 500 |
|  | 1000 |
| Ketoconazole | 150 |
|  | 300 |
| Flutamide | 50 |
|  | 150 |
| Carbamazepine | 150 |
|  | 300 |
| Ticlopidine | 150 |
|  | 300 |
| Metapyrilene | 50 |
|  | 150 |
| Chlorzoxasone | 500 |
|  | 1000 |
| Cyclosporine A | 50 |
|  | 100 |
| Bendazac | 300 |
|  | 1000 |
| 1-naphthyl isothiocyanate (ANIT) | 15 |
|  | 50 |
| Valproate | 350 |
|  | 700 |
| Tetracycline | 1000 |
|  | 2000 |
| Nimesulide | 100 |
|  | 200 |
| DL Ethionine | 125 |
|  | 250 |
| Carbon tetrachloride | 100 |
|  | 300 |

TABLE 4

Classification of toxic effects of drugs on liver histopathology according to the type of histopathology observed.

| Histopathology | Drug/Toxicant | Dose |
|---|---|---|
| Necrosis | Acetaminophen | High |
|  | Methapyrilene | High |
|  | Ticlopidine | High |
|  | Bendazac | High |
| Steatosis | Tetracycline | High |
|  | Carbon tetrachloride | High |
|  | Ethionine | High |
| Cholestasis | Cyclosporine A | High |
|  | ANIT | High |
| Phospholipidosis | Ketoconazole | High |
| No Histopathology | Valproate (ip) | High |
|  | Carbamazepine | High |
|  | Flutamide | High |
|  | Chlorzoxasone | High |
|  | Nimesulide | High |

The results of the liver histopathology and the routine clinical chemistry (i.e., aspartate aminotransferase (AST), alanine aminotransferase (ALT), total bilirubin (TBIL), and alkaline phosphatase (ALP)) are shown in Table 5. "~" indicates that the changes in histopathology or clinical chemistry were measured in some subjects but not all subjects at that time point, and "−" indicates the changes were not detected at either time point (day 2 or day 5).

TABLE 5

Effects of drug toxicants on histopathology and clinical chemistry.

| Drug/Toxicant | Dose | Histopathology | AST | ALT | TBIL | ALP |
|---|---|---|---|---|---|---|
| | | Necrosis | | | | |
| Acetaminophen | Low | Day2 | — | Day2 | Day2 | — |
| | High | Day2 | Day2 | Day2 | Day2 | — |
| Methapyrilene | L | Day5 | Day5 | Day5 | Day5 | — |
| | H | Day2~ | Day2~ | Day2~ | Day2~ | Day5 |
| Ticlopidine | L | — | — | Day2 | Day5 | — |
| | H | Day5 | — | Day5 | Day2~ | — |
| Bendazac | L | Day5 | — | Day5 | — | Day2 |
| | H | Day5 | — | Day5 | — | Day2~ |
| | | Steatosis | | | | |
| Tetracycline | L | Day2~ | — | — | — | — |
| | H | Day5 | — | — | — | — |
| Carbon tetrachloride | L | Day2~ | — | — | — | — |
| | H | Day2~ | — | — | — | — |
| Ethionine | L | Day2 | — | — | Day2~ | — |
| | H | Day2~ | — | — | Day2~ | — |
| | | Cholestasis | | | | |
| Cyclosporine A | L | — | — | — | Day2~ | — |
| | H | — | — | — | Day2~ | — |
| ANIT | L | Day5 | — | Day5 | Day5 | — |
| | H | Day2~ | Day2~ | Day2~ | Day2~ | — |
| | | None | | | | |
| Valproate (ip) | L | — | — | — | — | — |
| | H | — | — | — | — | — |
| Carbamazepine | L | — | — | — | — | — |
| | H | — | — | — | — | — |
| Flutamide | L | — | — | — | — | — |
| | H | — | — | — | Day2 | — |
| Chlorzoxasone | L | — | — | — | Day5 | — |
| | H | — | — | — | Day5 | — |
| Nimesulide | L | — | — | Day5 | Day2 | — |
| | H | — | — | — | Day2 | — |

As shown above, the toxicants carbamazepine, chlorzoxasone, flutamide, nimesulide, and valproate were classified as "No Rat Tox/Human specific" and had no hepatotoxic changes. That is, carbamazepine, chlorzoxasone, flutamide, nimesulide, and valproate are known hepatotoxins to humans, but were confirmed in this Example not to induce rat toxicity. Thus, based on this category of toxicant, as discussed below, biomarkers were discovered that are indicative of liver toxicity in humans but for which there is no associated histopathology or clinical chemistry change in rats. Such biomarkers are valuable to estimate the chemical's potential to cause human specific hepatotoxicity. These markers are useful to screen drugs for toxic effects in rats during pre-clinical drug development and to screen other agents (e.g., agriculture pesticides) in rats for toxic effects on the liver in humans.

The plasma, urine, and liver samples were analyzed for the levels of all biochemicals that were detectable in the samples, and were measured using a non-targeted global biochemical profiling analytical platform using biochemical profiling using methods described in U.S. Pat. Nos. 7,635,556; 7,433,686; 7,561,975; and U.S. Patent Publication No. 2009/0179147, all of which are incorporated herein by reference in their entirety. Biochemicals that are associated with liver toxicity are presented in Table 18.

Using the vehicle only group as a control (i.e., to determine the reference standard level for each biomarker), the analysis of the levels of the biochemicals from urine, plasma, and liver tissue revealed biomarkers that were differentially present (increase or decrease, $p<0.05$) between liver toxicity and no liver toxicity. In addition, biomarkers were discovered that are indicative of liver toxicity in humans but for which there is no associated histopathology or clinical chemistry change in rats. Statistical analysis using the t-test was performed to identify those biomarkers that changed significantly ($p<0.05$) in response to the drug and were associated with toxicity. The association with toxicity was determined by analyzing the biomarker data across all drugs to distinguish biomarkers for toxicity from other drug responses (e.g., therapeutic response). The results were also analyzed relative to fasting subjects to eliminate biomarkers that result from the effects of decreased feeding which is a common response to drug treatment. In particular, the following groups of biomarkers were discovered:

1. Biomarkers in urine that are indicative of liver toxicity (listed in Table 6);
2. Biomarkers in urine that are indicative of necrosis (listed in Table 7);
3. Biomarkers in urine that are indicative of cholestasis and/or steatosis (listed in Table 8);
4. Biomarkers in urine that are indicative of liver toxicity in humans but for which there is no associated histopathology or clinical chemistry change in rats (listed in Table 9);
5. Biomarkers in plasma that are indicative of liver toxicity (listed in Table 10);
6. Biomarkers in plasma that are indicative of necrosis (listed in Table 11);

7. Biomarkers in plasma that are indicative of cholestasis and/or steatosis (listed in Table 12);
8. Biomarkers in plasma that are indicative of liver toxicity in humans but for which there is no associated histopathology or clinical chemistry change in rats (listed in Table 13);
9. Biomarkers in liver tissue that are indicative of liver toxicity (listed in Table 14);
10. Biomarkers in liver tissue that are indicative of necrosis (listed in Table 15);
11. Biomarkers in liver tissue that are indicative of cholestasis and/or steatosis (listed in Table 16); and
12. Biomarkers in liver tissue that are indicative of liver toxicity in humans but for which there is no associated histopathology or clinical chemistry change in rats (listed in Table 17).

The biomarkers that change significantly ($p<0.05$, according to the t-test) with the type of toxin (e.g., steatosis, cholestasis, necrosis) are biomarkers for determining the type of toxicity induced by the toxin. These biomarkers increase or decrease in a manner that is characteristic for the type of liver toxicity caused by the agent.

TABLE 6

Liver toxicity biomarkers in urine
Liver Toxicity Biomarkers in Urine:

1,5-anhydroglucitol (1,5-AG)
2-(4-hydroxyphenyl)propionate
2'-deoxycytidine
2-methylbutyrylglycine
3-(4-hydroxyphenyl)lactate
3-dehydrocholate
3-hydroxy-2-ethylpropionate
4-ethylphenylsulfate
4-hydroxybutyrate (GHB)
4-imidazoleacetate
4-vinylphenol sulfate
5-hydroxyhexanoate
alpha-ketoglutarate
Anthranilate
beta-hydroxyisovalerate
catechol sulfate
Cholate
Citrate
Dimethylglycine
Glycocholate
Lactate
Malate
Mannose
N-acetylaspartate (NAA)
p-cresol sulfate
phenol sulfate
phenyllactate (PLA)
Pyroglutamine
sarcosine (N-Methylglycine)
Succinate
Taurine
Taurocholate
Threonine
trans-4-hydroxyproline
Tyramine
Metabolite - 03249_200
Metabolite - 06126_201
Metabolite - 10266
Metabolite - 10375
Metabolite - 10379
Metabolite - 10381
Metabolite - 10389
Metabolite - 11075
Metabolite - 11098
Metabolite - 11362
Metabolite - 12024
Metabolite - 12040
Metabolite - 12160
Metabolite - 12175

TABLE 6-continued

Liver toxicity biomarkers in urine
Liver Toxicity Biomarkers in Urine:

Metabolite - 12182
Metabolite - 12183
Metabolite - 12184
Metabolite - 12185
Metabolite - 12210
Metabolite - 12214
Metabolite - 12215
Metabolite - 12217
Metabolite - 12230
Metabolite - 12241
Metabolite - 12292
Metabolite - 12293
Metabolite - 12301
Metabolite - 12306
Metabolite - 12307
Metabolite - 12323
Metabolite - 12327
Metabolite - 12361
Metabolite - 12400
Metabolite - 12405
Metabolite - 12408
Metabolite - 12409
Metabolite - 12410
Metabolite - 12411
Metabolite - 12414
Metabolite - 13724
Metabolite - 13862
Metabolite - 14042
Metabolite - 14631
Metabolite - 14659
Metabolite - 4504
Metabolite - 6976

TABLE 7

Liver Toxicity Biomarkers in Urine that are indicative of liver Necrosis

| BIOCHEMICAL NAME (Necrosis biomarker list/urine) | Change with toxicity |
| --- | --- |
| threonine | Increase |
| 2-methylbutyrylglycine | Decrease |
| pyroglutamine | Increase |
| phenyllactate (PLA) | Increase |
| p-cresol sulfate | Decrease |
| 3-(4-hydroxyphenyl)lactate | Increase |
| tyramine | Decrease |
| phenol sulfate | Decrease |
| alpha-ketoglutarate | Decrease |
| malate | Decrease |
| cholate | Increase |
| 2'-deoxycytidine | Decrease |
| catechol sulfate | Decrease |
| 4-ethylphenylsulfate | Decrease |
| 4-vinylphenol sulfate | Decrease |
| Metabolite - 06126_201 | Decrease |
| Metabolite - 10266 | Decrease |
| Metabolite - 11098 | Decrease |
| Metabolite - 12024 | Decrease |
| Metabolite - 12040 | Decrease |
| Metabolite - 12160 | Decrease |
| Metabolite - 12182 | Decrease |
| Metabolite - 12183 | Decrease |
| Metabolite - 12184 | Decrease |
| Metabolite - 12185 | Decrease |
| Metabolite - 12214 | Decrease |
| Metabolite - 12215 | Decrease |
| Metabolite - 12230 | Decrease |
| Metabolite - 12241 | Decrease |
| Metabolite - 12307 | Decrease |
| Metabolite - 12323 | Decrease |
| Metabolite - 12327 | Decrease |
| Metabolite - 12400 | Decrease |
| Metabolite - 12405 | Decrease |

TABLE 7-continued

Liver Toxicity Biomarkers in Urine that are indicative of liver Necrosis

| BIOCHEMICAL NAME (Necrosis biomarker list/urine) | Change with toxicity |
|---|---|
| Metabolite - 12409 | Decrease |
| Metabolite - 12410 | Decrease |
| Metabolite - 12414 | Decrease |
| Metabolite - 13724 | Decrease |
| Metabolite - 14631 | Decrease |
| Metabolite - 14659 | Decrease |

TABLE 8

Liver toxicity Biomarkers in Urine that are indicative of Cholestasis and/or Steatosis

| BIOCHEMICAL NAME (steatosis, cholestasis biomarker list/urine) | Change with toxicity (Cholestasis) | Change with toxicity (Steatosis) |
|---|---|---|
| threonine | Increase | Increase |
| N-acetylaspartate (NAA) | Decrease | Decrease |
| pyroglutamine | Increase | Increase |
| 2-(4-hydroxyphenyl)propionate | Decrease | Decrease |
| anthranilate | Decrease | Decrease |
| beta-hydroxyisovalerate | Decrease | Decrease |
| 3-hydroxy-2-ethylpropionate | Decrease | Increase |
| taurine | No change | Increase |
| sarcosine (N-Methylglycine) | Decrease | Decrease |
| dimethylglycine | Decrease | Decrease |
| trans-4-hydroxyproline | Decrease | No Change |
| mannose | Increase | No Change |
| 1,5-anhydroglucitol (1,5-AG) | Increase | Decrease |
| lactate | Decrease | Decrease |
| citrate | Decrease | Decrease |
| alpha-ketoglutarate | Decrease | Decrease |
| succinate | Decrease | Decrease |
| malate | Decrease | Decrease |
| 4-hydroxybutyrate (GHB) | Decrease | No Change |
| 5-hydroxyhexanoate | Decrease | Decrease |
| cholate | increase | Increase |
| glycocholate | Increase | No Change |
| taurocholate | Increase | increase/decrease |
| 3-dehydrocholate | Increase | No Change |
| catechol sulfate | Decrease | Decrease |
| 4-ethylphenylsulfate | Decrease | Decrease |
| 4-vinylphenol sulfate | Decrease | Decrease |
| Metabolite - 03249_200 | Increase | Increase |
| Metabolite - 06126_201 | Decrease | Decrease |
| Metabolite - 10375 | Decrease | increase/decrease |
| Metabolite - 10379 | Decrease | Decrease |
| Metabolite - 10381 | Decrease | Decrease |
| Metabolite - 10389 | Decrease | Decrease |
| Metabolite - 11075 | Decrease | Decrease |
| Metabolite - 11362 | Decrease | Decrease |
| Metabolite - 12175 | Decrease | Decrease |
| Metabolite - 12182 | Decrease | Decrease |
| Metabolite - 12183 | Decrease | Decrease |
| Metabolite - 12184 | Decrease | Decrease |
| Metabolite - 12185 | Decrease | Decrease |
| Metabolite - 12210 | Decrease | Decrease |
| Metabolite - 12217 | Decrease | Decrease |
| Metabolite - 12230 | Decrease | Decrease |
| Metabolite - 12292 | Decrease | Decrease |
| Metabolite - 12293 | Decrease | Decrease |
| Metabolite - 12301 | Decrease | Decrease |
| Metabolite - 12306 | Decrease | Decrease |
| Metabolite - 12400 | Decrease | Decrease |
| Metabolite - 12408 | Decrease | Decrease |
| Metabolite - 12410 | Decrease | Decrease |
| Metabolite - 12411 | Decrease | Decrease |
| Metabolite - 12414 | Decrease | Decrease |
| Metabolite - 13862 | Increase | Increase |
| Metabolite - 14042 | Decrease | Decrease |
| Metabolite - 4504 | Decrease | Decrease |
| Metabolite - 6976 | Decrease | Decrease |

TABLE 9

Liver Toxicity Biomarkers in Urine that are indicative of an agent that induces liver toxicity in humans but for which there is no associated histopathology or clinical chemistry change in rats.

| BIOCHEMICAL NAME (Human specific list/urine) | Change with toxicity |
|---|---|
| pyroglutamine | Increase |
| 4-imidazoleacetate | Increase |
| cholate | Increase |
| Metabolite - 12183 | Decrease |
| Metabolite - 12184 | Decrease |
| Metabolite - 12185 | Decrease |
| Metabolite - 12217 | Decrease |
| Metabolite - 12241 | Decrease |
| Metabolite - 12361 | Decrease |

TABLE 10

Liver toxicity markers measured in plasma
Plasma Liver Toxicity Biomarkers 3-dehydrocholate
5-oxoproline
cholate
gamma-glutamylalanine
gamma-glutamylleucine
gamma-glutamylphenylalanine
gamma-glutamylthreonine
gamma-muricholate
glycochenodeoxycholate
glycocholate
glycodeoxycholate
gulono-1,4-lactone
N4-acetylcytidine
ophthalmate
pantothenate
tauro-beta-muricholate
taurochenodeoxycholate
taurocholate
taurocholenate sulfate
taurolithocholate 3-sulfate
trans-4-hydroxyproline
Metabolite - 02029_201
Metabolite - 11442
Metabolite - 11549
Metabolite - 11634
Metabolite - 12174
Metabolite - 12478_200
Metabolite - 12556
Metabolite - 12644
Metabolite - 14626

TABLE 11

Liver Toxicity Biomarkers in Plasma that are indicative of Necrosis

| BIOCHEMICAL NAME (necrosis list/plasma) | Change in Liver Toxicity |
|---|---|
| trans-4-hydroxyproline | Decrease |
| 5-oxoproline | Increase |
| ophthalmate | Increase |
| cholate | Increase |
| glycocholate | Increase |
| 3-dehydrocholate | Increase |
| glycodeoxycholate | Increase |
| glycochenodeoxycholate | Increase |
| gulono-1,4-lactone | Increase |
| Metabolite - 12478_200 | Increase |

TABLE 12

Liver toxicity Biomarkers in Plasma that are indicative of Cholestasis and/or Steatosis

| BIOCHEMICAL NAME (cholestasis, steatosis list/plasma) | Cholestasis Change in Liver Toxicity | Steatosis Change in Liver Toxicity |
|---|---|---|
| gamma-glutamylleucine | Increase | Increase |
| gamma-glutamylphenylalanine | Increase | Increase |
| gamma-glutamylthreonine | Increase | No Change |
| gamma-glutamylalanine | Increase | No Change |
| cholate | Increase | Decrease |
| glycocholate (H) | Increase | Decrease |
| taurocholate | Increase | Increase |
| taurochenodeoxycholate | Increase | Increase |
| 3-dehydrocholate | Increase | Decrease |
| taurolithocholate 3-sulfate | Increase | No Change |
| gamma-muricholate | Increase | No Change |
| tauro-beta-muricholate | Increase | Inconsistent |
| taurocholenate sulfate | Increase | Increase |
| N4-acetylcytidine | Increase | Increase |
| pantothenate | Increase | No Change |
| Metabolite - 02029_201 | Increase | Increase |
| Metabolite - 11442 | Increase | Increase |
| Metabolite - 11549 | Increase | Increase |
| Metabolite - 11634 | Increase | Increase |
| Metabolite - 12174 | Increase | Increase |
| Metabolite - 12556 | Increase | Increase |
| Metabolite - 12644 | Increase | Increase |
| Metabolite - 14626 | Increase | Increase |

TABLE 13

Liver Toxicity Biomarkers in Plasma that are indicative of an agent that induces liver toxicity in humans but for which there is no associated histopathology or clinical chemistry change in rats.

| BIOCHEMICAL NAME (human specific list/plasma) | Change in Liver Toxicity |
|---|---|
| glycocholate | Increase |
| glycochenodeoxycholate | Increase |

Liver Biomarkers of Liver Toxicity

TABLE 14

Liver toxicity markers measured in liver
Liver Tox markers measured in Liver 10-nonadecenoate (19:1n9)
1-docosahexaenoylglycerol (1-monodocosahexaenoin)
2-aminobutyrate
2'-deoxyinosine
3-aminoisobutyrate
4-hydroxybutyrate (GHB)
7-alpha-hydroxycholesterol
Acetylcarnitine
alpha-tocopherol
Carnitine
Cystathionine
Cysteine
Cysteinylglycine
dihomo-linoleate (20:2n6)
eicosenoate (20:1n9 or 11)
gamma-glutamylisoleucine
gamma-glutamylleucine
gamma-glutamylvaline
glucarate (saccharate)
glucose-6-phosphate (G6P)
Glucuronate
Glycerate
Glycochenodeoxycholate
Glycocholate

TABLE 14-continued

Liver toxicity markers measured in liver
Liver Tox markers measured in Liver

Glycodeoxycholate
gulono-1,4-lactone
homoserine (homoserine lactone)
Hypotaurine
Hypoxanthine
Isobutyrylcarnitine
N1-methyladenosine
N-acetylserine
Ophthalmate
pentadecanoate (15:0)
Propionylcarnitine
Taurine
Taurocholate
taurocholenate sulfate
Taurodeoxycholate
Taurolithocholate
Xanthine
Xylitol
Metabolite - 11569
Metabolite - 11570
Metabolite - 11571
Metabolite - 11575
Metabolite - 11578
Metabolite - 11593
Metabolite - 11629
Metabolite - 11630
Metabolite - 11631
Metabolite - 11639
Metabolite - 11640
Metabolite - 11724
Metabolite - 12000
Metabolite - 12183
Metabolite - 12184
Metabolite - 12185
Metabolite - 12188
Metabolite - 12304
Metabolite - 13391
Metabolite - 13396
Metabolite - 13502
Metabolite - 14658
Metabolite - 4599
Metabolite - 6647

TABLE 15

Liver Toxicity Biomarkers in Liver that are indicative of an agent that causes Necrosis

| BIOCHEMICAL NAME (Necrosis list/Liver) | Change in Toxicity |
|---|---|
| N-acetylserine | Increase |
| cysteine | Increase |
| cystathionine | Increase |
| hypotaurine | Decrease |
| taurine | Decrease |
| 2-aminobutyrate | Increase |
| ophthalmate | Increase |
| cysteinylglycine | Increase |
| gamma-glutamylvaline | Increase |
| gamma-glutamylleucine | Increase |
| gamma-glutamylisoleucine | Increase |
| glycerate | Increase |
| glucose-6-phosphate (G6P) | Increase |
| glucuronate | Increase |
| pentadecanoate (15:0) | Decrease |
| 10-nonadecenoate (19:1n9) | Decrease |
| eicosenoate (20:1n9 or 11) | Decrease |
| dihomo-linoleate (20:2n6) | Decrease |
| 4-hydroxybutyrate (GHB) | Increase |
| acetylcarnitine | Increase |
| glycocholate | Increase |
| glycochenodeoxycholate | Increase |
| 7-alpha-hydroxycholesterol | Increase |

TABLE 15-continued

Liver Toxicity Biomarkers in Liver that are indicative of an agent that causes Necrosis

| BIOCHEMICAL NAME (Necrosis list/Liver) | Change in Toxicity |
|---|---|
| xanthine | Decrease |
| hypoxanthine | Increase |
| 2'-deoxyinosine | Increase |
| N1-methyladenosine | Increase |
| 3-aminoisobutyrate | Increase |
| gulono-1,4-lactone | Increase |
| glucarate (saccharate) | Increase |
| alpha-tocopherol | Decrease |
| Metabolite - 12183 | Decrease |
| Metabolite - 12184 | Decrease |
| Metabolite - 12185 | Decrease |
| Metabolite - 12188 | Decrease |
| Metabolite - 12304 | Decrease |
| Metabolite - 13391 | Increase |
| Metabolite - 13396 | Increase |
| Metabolite - 13502 | Increase |

TABLE 16

Liver toxicity Biomarkers in Liver that are indicative of Cholestasis and/or Steatosis

| BIOCHEMICAL NAME (steatosis, cholestasis list/Liver)) | Change in toxicity | |
|---|---|---|
| | Cholestasis | Steatosis |
| homoserine (homoserine lactone) | Increase | Increase |
| isobutyrylcarnitine | Increase | Decrease |
| propionylcarnitine | Increase | Decrease |
| taurine | Increase | Increase |
| ophthalmate | Increase | Decrease |
| carnitine | Increase | Increase |
| acetylcarnitine | Increase | Decrease |
| taurocholate | Increase | No change |
| taurodeoxycholate | Decrease | No change |
| glycodeoxycholate | Decrease | No change |
| taurolithocholate | Decrease | No change |
| taurocholenate sulfate | Increase | No change |
| 1-docosahexaenoylglycerol (1-monodocosahexaenoin) | No change | Increase |
| Metabolite - 11575 | Decrease | No change |
| Metabolite - 11578 | Decrease | No change |
| Metabolite - 11593 | Increase | Decrease |
| Metabolite - 11640 | Decrease | Decrease |
| Metabolite - 11724 | Decrease | Decrease |
| Metabolite - 12188 | Decrease | Decrease |
| Metabolite - 12304 | Decrease | Decrease |
| Metabolite - 14658 | Increase | No change |
| Metabolite - 4599 | Increase | No change |
| Metabolite - 6647 | Increase | No change |

TABLE 17

Liver Toxicity Biomarkers in Liver that are indicative of an agent that induces liver toxicity in humans but for which there is no associated histopathology or clinical chemistry change in rats.

| BIOCHEMICAL NAME (human specific list/Liver) | Change in Toxicity |
|---|---|
| xylitol | Increase |
| xanthine | Decrease |
| glucarate (saccharate) | Increase |
| Metabolite - 11569 | Increase |
| Metabolite - 11570 | Increase |
| Metabolite - 11571 | Increase |
| Metabolite - 11629 | Increase |
| Metabolite - 11630 | Increase |
| Metabolite - 11631 | Increase |

TABLE 17-continued

Liver Toxicity Biomarkers in Liver that are indicative of an agent that induces liver toxicity in humans but for which there is no associated histopathology or clinical chemistry change in rats.

| BIOCHEMICAL NAME (human specific list/Liver) | Change in Toxicity |
|---|---|
| Metabolite - 11639 | Increase |
| Metabolite - 12000 | Increase |

Example 2

Random Forest Analysis of Liver Toxicity

The biomarkers listed in Table: 18 were measured in various samples obtained from subjects that had received a toxic dose of a drug and subjects that received sham treatment. Random forest analyses were then used to classify individuals. The "Out-of-Bag" (OOB) Error rate gives an estimate of how accurately new observations can be predicted using the random forest model.

TABLE 18

List of Liver Toxicity Biomarkers Measured 1,5-anhydroglucitol (1,5-AG)
10-nonadecenoate (19:1n9)
12-dehydrocholate
1-docosahexaenoylglycerol (1-monodocosahexaenoin)
2-(4-hydroxyphenyl)propionate
2-aminobutyrate
2'-deoxycytidine
2'-deoxyinosine
2-methylbutyrylglycine
3-(4-hydroxyphenyl)lactate
3-aminoisobutyrate
3-dehydrocholate
3-hydroxy-2-ethylpropionate
4-ethylphenylsulfate
4-hydroxybutyrate (GHB)
4-imidazoleacetate
4-vinylphenol sulfate
5-hydroxyhexanoate
5-oxoproline
6-beta-hydroxylithocholate
7-alpha-hydroxycholesterol
Acetylcarnitine
alpha-ketoglutarate
alpha-muricholate
alpha-tocopherol
anthranilate
beta-hydroxyisovalerate
beta-muricholate
Carnitine
catechol sulfate
chenodeoxycholate
cholate
citrate
Cystathionine
Cysteine
Cysteinylglycine
dihomo-linoleate (20:2n6)
dimethylglycine
eicosenoate (20:1n9 or 11)
gamma-glutamylalanine
gamma-glutamylisoleucine
gamma-glutamylleucine
gamma-glutamylphenylalanine
gamma-glutamylthreonine
gamma-glutamylvaline
gamma-muricholate
glucarate (saccharate)
glucose-6-phosphate (G6P)
Glucuronate

TABLE 18-continued

List of Liver Toxicity Biomarkers Measured

Glycerate
glycochenodeoxycholate
glycocholate
glycodeoxycholate
gulono-1,4-lactone
homoserine (homoserine lactone)
hyodeoxycholate
Hypotaurine
Hypoxanthine
Isobutyrylcarnitine
lactate
malate
mannose
N1-methyladenosine
N4-acetylcytidine
N-acetylaspartate (NAA)
N-acetylserine
ophthalmate
pantothenate
p-cresol sulfate
pentadecanoate (15:0)
phenol sulfate
phenyllactate (PLA)
Propionylcarnitine
pyroglutamine
sarcosine (N-Methylglycine)
succinate
Taurine
tauro-beta-muricholate
taurochenodeoxycholate
taurocholate
taurocholenate sulfate
taurodeoxycholate
taurolithocholate
taurolithocholate 3-sulfate
threonine
trans-4-hydroxyproline
tyramine
Xanthine
Xylitol
Metabolite - 02029_201
Metabolite - 03249_200
Metabolite - 06126_201
Metabolite - 10266
Metabolite - 10375
Metabolite - 10379
Metabolite - 10381
Metabolite - 10389
Metabolite - 11075
Metabolite - 11098
Metabolite - 11362
Metabolite - 11442
Metabolite - 11549
Metabolite - 11569
Metabolite - 11570
Metabolite - 11571
Metabolite - 11575
Metabolite - 11578
Metabolite - 11593
Metabolite - 11629
Metabolite - 11630
Metabolite - 11631
Metabolite - 11634
Metabolite - 11639
Metabolite - 11640
Metabolite - 11724
Metabolite - 12000
Metabolite - 12024
Metabolite - 12040
Metabolite - 12160
Metabolite - 12174
Metabolite - 12175
Metabolite - 12182
Metabolite - 12183
Metabolite - 12183
Metabolite - 12184
Metabolite - 12184
Metabolite - 12185
Metabolite - 12185
Metabolite - 12188
Metabolite - 12210
Metabolite - 12214
Metabolite - 12215
Metabolite - 12217
Metabolite - 12230
Metabolite - 12241
Metabolite - 12292
Metabolite - 12293
Metabolite - 12301
Metabolite - 12304
Metabolite - 12306
Metabolite - 12307
Metabolite - 12323
Metabolite - 12327
Metabolite - 12361
Metabolite - 12400
Metabolite - 12405
Metabolite - 12408
Metabolite - 12409
Metabolite - 12410
Metabolite - 12411
Metabolite - 12414
Metabolite - 12478_200
Metabolite - 12556
Metabolite - 12644
Metabolite - 13391
Metabolite - 13396
Metabolite - 13502
Metabolite - 13724
Metabolite - 13862
Metabolite - 14042
Metabolite - 14626
Metabolite - 14631
Metabolite - 14658
Metabolite - 14659
Metabolite - 4504
Metabolite - 4599
Metabolite - 6647
Metabolite - 6976

Results of Determining Liver Toxicity from Urine Samples

The biomarkers listed in Table: 18 were measured in urine samples obtained from subjects that had received a toxic dose of a drug and subjects that received sham treatment (see Example 1). Using Random Forest analysis the subjects were classified as having drug-induced liver toxicity (tox) or no toxicity (control) with >97% accuracy.

Classification of Subjects Using Named and Unnamed Biomarker Compounds in Urine

|  |  | Actual | | |
| --- | --- | --- | --- | --- |
|  |  | Control | Tox | Class.error |
| Predicted | Control | 74 | 1 | 0.01333 |
|  | Tox | 3 | 66 | 0.04348 |
|  | Total | 77 | 67 |  |

OOB (Out of Bag) error rate: 2.78%

The named (unnamed Metabolites were not included) biomarkers listed in Table: 18 were measured in urine samples obtained from subjects that had received a toxic dose of a drug and subjects that received sham treatment (see Example 1). Using Random Forest analysis the subjects were classified as having drug-induced liver toxicity (tox) or no toxicity (control) with >96% accuracy.

Classification of Subjects Using Named Biomarker Compounds Only in Urine

|  |  | Actual | | |
|---|---|---|---|---|
|  |  | Control | Tox | Class.error |
| Predicted | Control | 73 | 2 | 0.026667 |
|  | Tox | 3 | 66 | 0.043478 |
|  | Total | 76 | 68 |  |

OOB (Out of Bag) error rate: 3.47%

Although this analysis is based on the list of metabolites in the table of liver toxicity biomarkers above, not all of the biomarkers were measured in the samples. The following compounds were not detected in urine samples:
1. 12-dehydrocholate
2. 6-beta-hydroxylithocholate
3. beta-muricholate
4. chenodeoxycholate
5. glycodeoxycholate
6. hyodeoxycholate
7. tauro-beta-muricholate
8. taurocholenate sulfate*
9. taurodeoxycholate
10. taurolithocholate
11. taurolithocholate 3-sulfate Results of Determining Liver Toxicity from Liver Samples The biomarkers listed in Table: 18 were measured in liver samples obtained from subjects that had received a toxic dose of a drug and subjects that received sham treatment (see Example 1). Using Random Forest analysis the subjects were classified as having drug-induced liver toxicity (tox) or no toxicity (control) with >95% accuracy.

Classification of Subjects Using Named and Unnamed Biomarker Compounds in Liver

|  |  | Actual | | |
|---|---|---|---|---|
|  |  | Control | Tox | Class.error |
| Predicted | Control | 73 | 2 | 0.026667 |
|  | Tox | 5 | 64 | 0.072464 |
|  | Total | 77 | 67 |  |

OOB error rate: 4.86%

The named biomarkers (unnamed Metabolites were not included) listed in Table: 18 were measured in liver samples obtained from subjects that had received a toxic dose of a drug and subjects that received sham treatment (see Example 1). Using Random Forest analysis the subjects were classified as having drug-induced liver toxicity (tox) or no toxicity (control) with >91% accuracy.

Classification of Subjects Using Named Biomarker Compounds Only in Liver

|  |  | Actual | | |
|---|---|---|---|---|
|  |  | Control | Tox | Class.error |
| Predicted | Control | 71 | 4 | 0.053333 |
|  | Tox | 9 | 60 | 0.130435 |
|  | Total | 80 | 64 |  |

OOB error rate: 9.0%

The following compounds in the list were not detected: gaurine and gaurocholate.

Results of Determining Liver Toxicity from Plasma Samples

Biomarkers listed in Table 18: Liver toxicity biomarkers were measured in plasma samples obtained from subjects that had received a toxic dose of a drug and subjects that received sham treatment (see Example 1). Using Random Forest analysis the subjects were classified as having drug-induced liver toxicity (tox) or no toxicity (control) with >86% accuracy.

Classification of Subjects Using Named and Unnamed Biomarker Compounds in Plasma

|  |  | Actual | | |
|---|---|---|---|---|
|  |  | Control | Tox | Class.error |
| Predicted | Control | 68 | 7 | 0.026667 |
|  | Tox | 12 | 57 | 0.072464 |
|  | Total | 80 | 64 |  |

OOB error rate: 13.2%

The named biomarkers (unnamed Metabolites were not included) listed in Table 18: Liver toxicity biomarkers were measured in plasma samples obtained from subjects that had received a toxic dose of a drug and subjects that received sham treatment (see Example 1). Using Random Forest analysis the subjects were classified as having drug-induced liver toxicity (tox) or no toxicity (control) with >88% accuracy.

Classification of Subjects Using Named Biomarker Compounds Only in Plasma

|  |  | Actual | | |
|---|---|---|---|---|
|  |  | Control | Tox | Class.error |
| Predicted | Control | 68 | 7 | 0.093333 |
|  | Tox | 9 | 60 | 0.130435 |
|  | Total | 77 | 67 |  |

OOB error rate: 11.11%

There were two compounds on the list that were not detected: chenodeoxycholate and Taurolithocholate.

Example 3

Random Forest Analysis of the Type of Liver Toxicity

The biomarkers listed in Table: 18 were measured in various samples obtained from subjects that had received a toxic dose of a drug that causes necrosis, steatosis or human specific effects. Random forest analyses were then used to classify individuals. The "Out-of-Bag" (OOB) Error rate gives an estimate of how accurately new observations can be predicted using the random forest model.

Results of Determining the Type of Liver Toxicity from Urine Samples

Biomarkers listed in Table 18: Liver toxicity biomarkers were measured in urine samples obtained from subjects that had received a toxic dose of a drug that causes necrosis, steatosis or human specific effects (see Example 1 and Table 4). Using Random Forest analysis the subjects were classified as having either human specific, necrosis or steatosis with ~91% accuracy using named and unnamed biomarkers and >93% accuracy using named biomarkers only.

Classification of Subjects Using Named and Unnamed Biomarker Compounds in Urine

|  |  | Actual | | | |
| --- | --- | --- | --- | --- | --- |
|  |  | Human Specific | Necrosis | Steatosis | Class.error |
| Predicted | Human Specific | 19 | 0 | 0 | 0 |
|  | Necrosis | 4 | 11 | 0 | 0.2666667 |
|  | Steatosis | 0 | 0 | 10 | 0 |
|  |  | 23 | 11 | 10 |  |

OOB error rate: 9.09%

Classification of Subjects Using Only Named Biomarker Compounds in Urine

|  |  | Actual | | | |
| --- | --- | --- | --- | --- | --- |
|  |  | Human Specific | Necrosis | Steatosis | Class.error |
| Predicted | Human Specific | 19 | 0 | 0 | 0 |
|  | Necrosis | 3 | 12 | 0 | 0.2 |
|  | Steatosis | 0 | 0 | 10 | 0 |
|  |  | 22 | 12 | 10 |  |

OOB error rate: 6.82%

Results of Determining the Type of Liver Toxicity from Liver Samples

Biomarkers listed in Table 18: Liver toxicity biomarkers were measured in liver samples obtained from subjects that had received a toxic dose of a drug that causes necrosis, steatosis or human specific effects (see Example 1 and Table 4). Using Random Forest analysis the subjects were classified as having either human specific, necrosis or steatosis with ~98% accuracy using named and unnamed biomarkers and ~98% accuracy using named biomarkers only.

Classification of Subjects Using Named and Unnamed Biomarker Compounds in Liver

|  |  | Actual | | | |
| --- | --- | --- | --- | --- | --- |
|  |  | Human Specific | Necrosis | Steatosis | Class.error |
| Predicted | Human Specific | 19 | 0 | 0 | 0 |
|  | Necrosis | 1 | 14 | 0 | 0.066667 |
|  | Steatosis | 0 | 0 | 10 | 0 |
|  |  | 20 | 14 | 10 |  |

OOB error rate: 2.27%

Classification of Subjects Using Only Named Biomarker Compounds in Liver

|  |  | Actual | | | |
| --- | --- | --- | --- | --- | --- |
|  |  | Human Specific | Necrosis | Steatosis | Class.error |
| Predicted | Human Specific | 19 | 0 | 0 | 0 |
|  | Necrosis | 1 | 14 | 0 | 0.066667 |
|  | Steatosis | 0 | 0 | 10 | 0 |
|  |  | 20 | 14 | 10 |  |

OOB error rate: 2.27%

Results of Determining the Type of Liver Toxicity from Plasma Samples

Biomarkers listed in Table 18: Liver toxicity biomarkers were measured in plasma samples obtained from subjects that had received a toxic dose of a drug that causes necrosis, steatosis or human specific effects (see Example 1 and Table 4). Using Random Forest analysis the subjects were classified as having either human specific, necrosis or steatosis with ~91% accuracy using named and unnamed biomarkers and >88% accuracy using named biomarkers only.

Classification of Subjects Using Named and Unnamed Biomarker Compounds in Plasma

|  |  | Actual | | | |
| --- | --- | --- | --- | --- | --- |
|  |  | Human Specific | Necrosis | Steatosis | Class.error |
| Predicted | Human Specific | 18 | 0 | 1 | 0.052632 |
|  | Necrosis | 3 | 12 | 0 | 0.2 |
|  | Steatosis | 0 | 0 | 10 | 0 |
|  |  | 21 | 12 | 11 |  |

OOB error rate: 9.09%

Classification of Subjects Using Only Named Biomarker Compounds in Plasma

|  |  | Actual | | | |
| --- | --- | --- | --- | --- | --- |
|  |  | Human Specific | Necrosis | Steatosis | Class.error |
| Predicted | Human Specific | 17 | 1 | 1 | 0.1052632 |
|  | Necrosis | 3 | 12 | 0 | 0.2 |
|  | Steatosis | 0 | 0 | 10 | 0 |
|  |  | 20 | 13 | 11 |  |

OOB error rate: 11.36%

Example 4

Dansylation Assay

Described below is a prophetic dansylation assay.

Dansylation products generally show a significant signal enhancement in reversed phase ESI- and APCI-LC-MS compared to the genuine analyte species. The enhancement is due to increased ionization through introduction of a basic dimethylamino moiety and increased hydrophobicity of the dansylation product. The basic dimethylamino improves protonation of the analyte. The higher hydrophobicity facilitates elution at a higher organic solvent content of the mobile phase under reversed phase conditions. This higher content of volatile organic solvents enhances ionization through faster and better evaporation of the mobile phase in the LC-MS interface. Urine is spiked with internal standards and derivatized with dansyl chloride. Plasma samples are first subjected to protein precipitation and a portion of the extract is derivatized with dansyl chloride. An aliquot of the reaction mixture is directly injected without further processing onto a LC-MS-MS system equipped with a reversed phase U-HPLC column.

The peak areas of the respective analyte product ions are measured against the peak area of the product ions of the internal standards. Quantitation is performed using a weighted linear least squares regression analysis.

Procedure:

Urine:

20.0 µL of a urine sample is placed into a crimp-cap glass vial. 20.0 µL of internal standard solution are added. Then, 20.0 µL of sodium bicarbonate solution (0.1 M) is added, followed by 50.0 µL of dansyl chloride solution (2 mg/mL in acetone). Vials are crimp capped; the content is mixed and subsequently heated at 60 C for 10 min. Then, vials are centrifuged and an aliquot of the reaction mixture is analyzed by LC-MS-MS.

Plasma:

20.0 µL of a plasma sample is placed into a glass vial. 20.0 µL of internal standard solution are added. To precipitate proteins 400 µL of methanol are added. The samples are mixed and subsequently centrifuged. To 50.0 µL of the clear supernatant, 20.0 µL of sodium bicarbonate solution (0.1 M) is added, followed by 50.0 µL of dansyl chloride solution (2 mg/mL in acetone). Vials are crimp capped; the content is mixed and subsequently heated at 60 C for 10 min. Then, vials are centrifuged and an aliquot of the reaction mixture is analyzed by LC-MS-MS.

Hepatocytes:

20.0 µL of a hepatocyte sample is placed into a glass vial. 20.0 µL of internal standard solution are added. To precipitate proteins 400 µL of methanol are added. The samples are mixed and subsequently centrifuged. To 50.0 µL of the clear supernatant, 20.0 µL of sodium bicarbonate solution (0.1 M) is added, followed by 50.0 µL of dansyl chloride solution (2 mg/mL in acetone). Vials are crimp capped; the content is mixed and subsequently heated at 60 C for 10 min. Then, vials are centrifuged and an aliquot of the reaction mixture is analyzed by LC-MS-MS.

Example 5

In vitro Assays with Known Hepatotoxic Agent

Hepatocytes are exposed to a hepatoxicant selected from Table 2 at various levels of the agent that have increasingly hepatotoxic effects (for example, acetaminophen at 0 (control), 500, 1000 mg/kg) as described in Table 3. Cells are harvested at various times after administration of the toxicant (e.g., day 2 and day 5), for the global non-targeted analysis of all biochemicals that can be measured in the samples, including the biochemicals listed in Table(s) 1 and/or 2 (i.e., toxicity biomarkers).

Example 6

Determination of Hepatotoxicity of a Test Agent

Prophetic Examples of In vitro and In vivo Assays that Could be Performed are Described Below.

In vitro Assays.

Hepatocytes are exposed to an agent. Samples are collected at various times after the agent is administered for analysis. The levels of each biochemical in the panel of hepatotoxicity biochemicals listed in Table(s) 1 and/or 2 are determined for the sample. The levels are input into a classifier associated with the panel. An output is obtained from the classifier, the output indicative of whether liver toxicity has occurred. The output is an index of hepatotoxicity of the agent and is reported as a hepatotoxicity score for that agent.

In vivo Assays.

A subject (e.g., mouse, rat, dog, human, mammal) is exposed to an agent. Samples are collected at various times after the agent is administered for analysis. The samples are blood, serum, and/or urine. The levels of each biochemical in the panel of hepatotoxicity biochemicals listed in Table(s) 1 and/or 2 are determined for the sample. The levels are input into a classifier associated with the panel. An output is obtained from the classifier, the output indicative of whether liver toxicity has occurred in the subject. The output is an index of hepatotoxicity of the agent and is reported as a hepatotoxicity score for that agent.

Example 7

Analytical Characterization of Unnamed Biomarkers Compounds

Table 19 below includes analytical characteristics of each of the unnamed metabolites listed in the Tables above. Methods for the analysis of metabolites using LC-MS techniques are provided in U.S. Pat. Nos. 7,433,787 and 7,561,975, U.S. Patent Publication 20090017464 and using GC-MS techniques are provided in Lawton, et al. Pharmacogenomics 9(4): 383-397 (2008). The table includes, for each listed Metabolite, the retention time (RT), retention index (RI), mass, and polarity obtained using the analytical methods described above. "Mass" refers to the mass of the C12 isotope of the parent ion used in quantification of the compound. "Polarity" indicates the polarity of the quantitative ion as being either positive (+) or negative (−). "Platform" indicates the compound was measured using GS/MS or LC/MS/MS.

TABLE 19

Analytical Characteristics of Unnamed Metabolites.

| NAME | Platform | COMP_ID | RT | RI | Mass | Polarity |
|---|---|---|---|---|---|---|
| Metabolite - 4504 | GC/MS | 16831 | 8.46 | 1597.1 | 244.10 | + |
| Metabolite - 4599 | GC/MS | 16984 | 7.42 | 1471.1 | 113.00 | + |
| Metabolite - 6647 | GC/MS | 19596 | 9.13 | 1696.7 | 197.10 | + |
| Metabolite - 6976 | GC/MS | 20004 | 12.97 | 2107.6 | 202.10 | + |
| Metabolite - 10266 | GC/MS | 24469 | 9.17 | 1655.0 | 328.00 | + |

TABLE 19-continued

Analytical Characteristics of Unnamed Metabolites.

| NAME | Platform | COMP_ID | RT | RI | Mass | Polarity |
|---|---|---|---|---|---|---|
| Metabolite - 10375 | GC/MS | 25439 | 12.47 | 2033.0 | 375.10 | + |
| Metabolite - 10379 | GC/MS | 25443 | 12.82 | 2075.0 | 375.00 | + |
| Metabolite - 10381 | GC/MS | 25445 | 12.94 | 2087.0 | 375.00 | + |
| Metabolite - 10389 | GC/MS | 25453 | 13.98 | 2223.0 | 290.00 | + |
| Metabolite - 11075 | GC/MS | 32030 | 11.59 | 1958.0 | 209.10 | + |
| Metabolite - 11098 | GC/MS | 32122 | 8.39 | 1595.0 | 271.20 | + |
| Metabolite - 12556 | GC/MS | 34123 | 6.61 | 1374.0 | 116.90 | + |
| Metabolite - 14042 | GC/MS | 35955 | 7.06 | 1420.0 | 158.10 | + |
| Metabolite - 03249_200 | LC/MS/MS | 32653 | 1.03 | 1049.0 | 141.10 | + |
| Metabolite - 11362 | LC/MS/MS | 32679 | 1.86 | 1906.0 | 344.00 | + |
| Metabolite - 11569 | LC/MS/MS | 32886 | 1.22 | 1228.0 | 338.00 | + |
| Metabolite - 11570 | LC/MS/MS | 32887 | 1.38 | 1417.0 | 470.10 | + |
| Metabolite - 11571 | LC/MS/MS | 32888 | 1.39 | 1432.0 | 440.10 | + |
| Metabolite - 11575 | LC/MS/MS | 32892 | 1.78 | 1799.0 | 264.10 | + |
| Metabolite - 11578 | LC/MS/MS | 32895 | 2.12 | 2146.0 | 298.10 | + |
| Metabolite - 11724 | LC/MS/MS | 33069 | 1.17 | 1184.0 | 997.90 | + |
| Metabolite - 12000 | LC/MS/MS | 33346 | 4.00 | 4024.0 | 434.10 | + |
| Metabolite - 12160 | LC/MS/MS | 33577 | 0.89 | 916.0 | 290.20 | + |
| Metabolite - 12174 | LC/MS/MS | 33595 | 3.06 | 3165.0 | 431.10 | + |
| Metabolite - 12241 | LC/MS/MS | 33663 | 1.38 | 1455.0 | 242.10 | + |
| Metabolite - 12361 | LC/MS/MS | 33789 | 4.56 | 4563.0 | 409.00 | + |
| Metabolite - 12478_200 | LC/MS/MS | 33924 | 4.93 | 4975.0 | 464.10 | + |
| Metabolite - 13391 | LC/MS/MS | 35091 | 3.92 | 3975.0 | 204.10 | + |
| Metabolite - 13396 | LC/MS/MS | 35099 | 5.13 | 5153.0 | 246.20 | + |
| Metabolite - 13502 | LC/MS/MS | 35276 | 0.86 | 874.0 | 306.10 | + |
| Metabolite - 06126_201 | LC/MS/MS | 32557 | 2.69 | 2684.0 | 203.10 | − |
| Metabolite - 11442 | LC/MS/MS | 32759 | 3.91 | 3902.0 | 331.10 | − |
| Metabolite - 11549 | LC/MS/MS | 32866 | 5.11 | 5093.0 | 339.30 | − |
| Metabolite - 11593 | LC/MS/MS | 32910 | 0.79 | 790.0 | 189.20 | − |
| Metabolite - 11629 | LC/MS/MS | 32946 | 3.32 | 3313.0 | 462.20 | − |
| Metabolite - 11630 | LC/MS/MS | 32947 | 3.39 | 3379.0 | 462.10 | − |
| Metabolite - 11631 | LC/MS/MS | 32948 | 3.44 | 3438.0 | 462.10 | − |
| Metabolite - 11634 | LC/MS/MS | 32951 | 3.60 | 3597.0 | 255.30 | − |
| Metabolite - 11639 | LC/MS/MS | 32956 | 3.70 | 3688.0 | 432.20 | − |
| Metabolite - 11640 | LC/MS/MS | 32957 | 3.78 | 3776.0 | 377.10 | − |
| Metabolite - 02029_201 | LC/MS/MS | 32966 | 4.83 | 4810.0 | 512.30 | − |
| Metabolite - 12024 | LC/MS/MS | 33370 | 1.88 | 1900.0 | 207.10 | − |
| Metabolite - 12040 | LC/MS/MS | 33391 | 0.95 | 942.0 | 259.00 | − |
| Metabolite - 12175 | LC/MS/MS | 33596 | 3.12 | 3161.0 | 297.20 | − |
| Metabolite - 12182 | LC/MS/MS | 33603 | 2.75 | 2789.0 | 208.20 | − |
| Metabolite - 12183 | LC/MS/MS | 33604 | 2.62 | 2651.0 | 208.20 | − |
| Metabolite - 12184 | LC/MS/MS | 33605 | 3.61 | 3645.0 | 337.10 | − |
| Metabolite - 12185 | LC/MS/MS | 33606 | 3.48 | 3520.0 | 337.10 | − |
| Metabolite - 12188 | LC/MS/MS | 33609 | 2.83 | 2866.0 | 228.20 | − |
| Metabolite - 12210 | LC/MS/MS | 33631 | 2.22 | 2238.0 | 336.10 | − |
| Metabolite - 12214 | LC/MS/MS | 33635 | 1.95 | 1973.0 | 242.10 | − |
| Metabolite - 12215 | LC/MS/MS | 33636 | 2.78 | 2815.0 | 333.00 | − |
| Metabolite - 12217 | LC/MS/MS | 33638 | 2.32 | 2343.0 | 203.10 | − |
| Metabolite - 12230 | LC/MS/MS | 33652 | 3.32 | 3360.0 | 217.10 | − |
| Metabolite - 12292 | LC/MS/MS | 33714 | 1.55 | 1573.0 | 342.10 | − |
| Metabolite - 12293 | LC/MS/MS | 33715 | 1.61 | 1626.0 | 258.10 | − |
| Metabolite - 12301 | LC/MS/MS | 33723 | 1.95 | 1973.0 | 240.10 | − |
| Metabolite - 12304 | LC/MS/MS | 33726 | 2.75 | 2789.0 | 200.20 | − |
| Metabolite - 12306 | LC/MS/MS | 33728 | 2.34 | 2364.0 | 247.10 | − |
| Metabolite - 12307 | LC/MS/MS | 33729 | 2.10 | 2119.0 | 217.10 | − |
| Metabolite - 12323 | LC/MS/MS | 33745 | 1.31 | 1327.0 | 230.20 | − |
| Metabolite - 12327 | LC/MS/MS | 33749 | 3.37 | 3410.0 | 240.10 | − |
| Metabolite - 12400 | LC/MS/MS | 33828 | 2.48 | 2478.0 | 259.20 | − |
| Metabolite - 12405 | LC/MS/MS | 33833 | 2.55 | 2549.0 | 212.10 | − |
| Metabolite - 12408 | LC/MS/MS | 33836 | 1.78 | 1790.0 | 285.20 | − |
| Metabolite - 12409 | LC/MS/MS | 33837 | 0.95 | 957.0 | 261.10 | − |
| Metabolite - 12410 | LC/MS/MS | 33838 | 2.13 | 2130.0 | 274.10 | − |
| Metabolite - 12411 | LC/MS/MS | 33839 | 1.08 | 1077.0 | 195.20 | − |
| Metabolite - 12414 | LC/MS/MS | 33842 | 1.67 | 1677.0 | 205.10 | − |
| Metabolite - 12644 | LC/MS/MS | 34244 | 5.74 | 5650.0 | 524.30 | − |
| Metabolite - 13724 | LC/MS/MS | 35534 | 1.31 | 1330.0 | 243.00 | − |
| Metabolite - 13862 | LC/MS/MS | 35757 | 2.24 | 2263.0 | 250.10 | − |
| Metabolite - 14626 | LC/MS/MS | 36553 | 4.80 | 4856.0 | 288.80 | − |
| Metabolite - 14631 | LC/MS/MS | 36558 | 1.44 | 1475.0 | 246.10 | − |
| Metabolite - 14658 | LC/MS/MS | 36585 | 4.75 | 4812.0 | 288.80 | − |
| Metabolite - 14659 | LC/MS/MS | 36586 | 0.60 | 623.0 | 101.20 | − |

What is claimed is:

1. A method of aiding in predicting the effect of an agent on liver function in a subject, comprising:
   administering a test agent to a subject;
   measuring levels of all of the following biomarkers: 4-ethylphenylsulfate, 1,5-anhydroglucitol (1,5-AG), 10-nonadecenoate (19:1n9), 2-(4-hydroxyphenyl)propionate, 2'deoxycytidine, 2-methylbutyrylglycine, 3-(4-hydroxyphenyl)lactate, 3-dehydrocholate, 3-hydroxy-2-ethylpropionate,4-hydroxybutyrate (GHB), 4-imidazoleacetate, 4-vinylphenolsulfate, 5-hydroxyhexanoate, alpha-ketoglutarate, anthranilate, beta-hydroxyisovalerate, catechol sulfate, cholate, citrate, dimethylglycine, glycocholate, lactate, malate, mannose, N-acetylaspartate (NAA), p-cresol sulfate, phenol sulfate, phenyllactate (PLA), pyroglutamine, sarcosine (N-methylglycine), succinate, taurine, taurocholate, threonine, trans-4-hydroxyproline, tyramine, 5-oxoproline, gamma-glutamylalanine, gamma-glutamylleucine, gamma-glutamylphenylalanine, gamma-glutamylthreonine, gamma-muricholate, glycochenodeoxycholate, glycodeoxycholate, gulono-1,4-lactone, N4-acetylcytidine, opthalmate, pantothenate, tauro-beta-muricholate, taurochenodeoxycholate, taurocholenate sulfate, taurolithocholate 3-sulfate, 1-docosahexaenoylglycerol (1-monodocosahexaenoin), 2-aminobutyrate, 2'-deoxyinosine, 3-aminoisobutyrate, 7-alpha-hydroxycholesterol, acetylcarnitine, alpha-tocopherol, carnitine, cystathionine, cysteine, cysteinylglycine, diohomo-linoleate (20:2n6), eicosenoate (20:1n9 or 11), gamma-glutamylisoleucine, gamma-glutamylvaline, glucarate (saccharate), glucose-6-phosphate (G6P), glucuronate, glycerate, homoserine (homoserine lactone), hypotaurine, hypoxanthine, isobutyrylcarnitine, N1-methyladenosine, N-acetylserine, pentadecanoate (15:0), propionylcarnitine, taurodeoxycholate, taurolithocholate, xanthine, and xylitol in a biological sample obtained from the subject; and
   comparing the levels of the biomarkers in the sample to hepatotoxicity-positive and/or hepatotoxicity-negative reference levels of the biomarkers in order to predict the effect of the test agent on liver function in the subject.

2. The method of claim 1, wherein the subject is a mammal.

3. The method of claim 2, wherein the subject is a rat.

4. A method of aiding in predicting the effect of a test agent on liver function in a subject, comprising measuring levels of all of the following biomarkers: 4-ethylphenylsulfate, 1,5-anhydroglucitol (1,5-AG), 2-(4-hydroxyphenyl)propionate, 2'deoxycytidine, 2-methylbutyrylglycine, 3-(4-hydroxyphenyl)lactate, 3-dehydrocholate, 3-hydroxy-2-ethylpropionate, 4-hydroxybutyrate (GHB), 4-imidazoleacetate, 4-vinylphenol sulfate, 5-hydroxyhexanoate, alpha-ketoglutarate, anthranilate, beta-hydroxyisovalerate, catechol sulfate, cholate, citrate, dimethylglycine, glycocholate, lactate, malate, mannose, N-acetylaspartate (NAA), p-cresol sulfate, phenol sulfate, phenyllactate (PLA), pyroglutamine, sarcosine (N-methylglycine), succinate, taurine, taurocholate, threonine, trans-4-hydroxyproline, and tyramine in a urine sample obtained from a subject to whom a test agent has been administered, and
   comparing the levels of the biomarkers in the sample to hepatotoxicity-positive and/or hepatotoxicity-negative reference levels of the biomarkers in order to predict the effect of the test agent on liver function in the subject.

5. The method of claim 4, wherein a decrease in the level of 2'-deoxycytidine, 2-methylbutyrylglycine, 4-ethylphenylsulfate, 4-vinylphenol sulfate, alpha-ketoglutarate, catechol sulfate, malate, p-cresol sulfate, phenol sulfate, and tyramine and an increase in the level of 3-(4-hydroxyphenyl)lactate, cholate, phenyllactate (PLA), pyroglutamine, and threonine is indicative of necrosis of the liver in the subject.

6. The method of claim 4, wherein an increase in the level of threonine, cholate, and taurocholate and a decrease in the level of 2-(4-hydroxyphenyl)propionate, 4-ethylphenylsulfate, 4-vinylphenolsulfate, 5-hydroxyhexanoate, alpha ketoglutarate, anthranilate, beta-hydroxyisovalerate, catechol sulfate, citrate, dimethylglycine, lactate, malate, N-acetylaspartate (NAA), sarcosine (N-methylglycine), and succinate is indicative of cholestasis and/or steatosis of the liver in the subject.

7. The method of claim 4, wherein an increase in the level of 4-imidazoleacetate, cholate, and pyroglutamine is indicative of damage to liver function in a human subject.

8. A method of aiding in predicting the effect of a test agent on liver function in a subject, comprising measuring levels of all of the following biomarkers: 3-dehydrocholate, 5-oxoproline, cholate, gamma-glutamylalanine, gamma-glutamylleucine, gamma-glutamylphenylalanine, gamma-glutamylthreonine, gamma-muricholate, glycochenodeoxycholate, glycocholate, glycodeoxycholate, gulono-1,4-lactone, N4-acetylcytidine, opthalmate, pantothenate, tauro-beta-muricholate, taurochenodeoxycholate, taurocholate, taurocholenate sulfate, taurolithocholate 3-sulfate, and trans-4-hydroxyproline in a plasma sample obtained from a subject to whom a test agent has been administered, and
   comparing the levels of the biomarkers in the sample to hepatotoxicity-positive and/or hepatotoxicity-negative reference levels of the biomarkers in order to predict the effect of the test agent on liver function in the subject.

9. The method of claim 8, wherein a decrease in the level of trans-4-hydroxyproline and an increase in the level of 3-dehydrocholate, 5-oxoproline, cholate, glycochenodeoxycholate, glycocholate, glycodeoxycholate, gulono-1,4-lactone, and opthalmate is indicative of necrosis of the liver in the subject.

10. The method of claim 8, wherein an increase in the level of gamma-glutamylleucine, gamma-glutamylphenylalanine, taurocholate, taurochenodeoxycholate, taurocholenate sulfate, and N4-acetylcytidine is indicative of cholestasis and/or steatosis of the liver in the subject.

11. The method of claim 8, wherein an increase in the level of glycocholate and glycochenodeoxycholate is indicative of damage to liver function in a human subject.

12. A method of aiding in predicting the effect of a test agent on liver function in a subject, comprising measuring the levels of all of the following biomarkers: 10-nonadecenoate (19:1n9), 1-docosahexaenoylglycerol (1-monodocosahexaenoin), 2-aminobutyrate, 2'-deoxyinosine, 3-aminoisobutyrate, 4-hydroxybutyrate (GHB), 7-alpha-hydroxycholesterol, acetylcarnitine, alpha-tocopherol, carnitine, cystathionine, cysteine, cysteinylglycine, diohomo-linoleate (20:2n6), eicosenoate (20:1n9 or 11), gamma-glutamylisoleucine, gamma-glutamylleucine, gamma-glutamylvaline, glucarate (saccharate), glucose-6-phosphate (G6P), glucuronate, glycerate, glycochenodeoxycholate, glycocholate, glycodeoxycholate, gulono-1,4-lactone, homoserine (homoserine lactone), hypotaurine, hypoxanthine, isobutyrylcarnitine, N1-methyladenosine, N-acetylserine, opthalmate, pentadecanoate (15:0), propionylcarnitine, taurine, taurocholate, taurocholate sulfate, taurodeoxycholate, taurolithocholate, xanthine, and xylitol in a liver tissue sample obtained from a subject to whom a test agent has been administered, and comparing the levels of the biomarkers in the sample to hepatotoxicity-positive and/or hepatotoxicity-negative reference levels of the biomarkers in order to predict the effect of the test agent on liver function in the subject.

13. The method of claim 12, wherein a decrease in the level of 10-nonadecenoate (19:1n9), alpha-tocopherol, dihomo-linoleate (20:2n6), eicosenoate (20:1n9 or 11), hypotaurine, pentadecanoate (15:0), taurine, and xanthine and an increase in the level of 2-aminobutyrate, 2'-deoxyinosine, 3-aminoisobutyrate, 4-hydroxybutyrate (GHB), 7-alpha-hydroxycholesterol, acetylcarnitine, cystathionine, cysteine, cysteinylglycine, gamma-glutamylvaline, gamma-glutamylleucine, gamma-glutamylisoleucine, glucarate (saccharate), glucose-6-phosphate (G6P), glycerate, glucuronate, glycochenodeoxycholate, glycocholate, gulono-1,4-lactone, hypoxanthine, N1-methyladenosine, N-acetylserine, and ophthalmate, is indicative of necrosis of the liver in the subject.

14. The method of claim 12, wherein an increase in the level of carnitine, homoserine (homoserine lactone), and taurine is indicative of cholestasis and/or steatosis of the liver in the subject.

15. The method of claim 12, wherein a decrease in the level of xanthine and an increase in the level of glucarate (saccharate) and xylitol is indicative of damage to liver function in a human subject.

* * * * *

UNITED STATES PATENT AND TRADEMARK OFFICE
CERTIFICATE OF CORRECTION

| | | |
|---|---|---|
| PATENT NO. | : 8,658,351 B2 | Page 1 of 1 |
| APPLICATION NO. | : 13/148082 | |
| DATED | : February 25, 2014 | |
| INVENTOR(S) | : Milburn et al. | |

It is certified that error appears in the above-identified patent and that said Letters Patent is hereby corrected as shown below:

In the Claims:

Column 33, claim 5, line 67, replace "4-ethvlphenylsul-" with --4-ethylphenylsul- --.

Signed and Sealed this
Twenty-seventh Day of May, 2014

Michelle K. Lee
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,658,351 B2 | Page 1 of 1 |
| APPLICATION NO. | : 13/148082 | |
| DATED | : February 25, 2014 | |
| INVENTOR(S) | : Milburn et al. | |

It is certified that error appears in the above-identified patent and that said Letters Patent is hereby corrected as shown below:

In the Specification:

Column 2, line 49, after "invention", insert --is--;

Column 2, line 64, after "level that is", insert --indicative of a lack of a particular disease state or phenotype. For example, a--;

Column 7, line 29, after "biomarker(s) in", insert --the--;

Column 7, line 63, after "biomarker(s) in", insert --the--;

Column 15, lines 18-19, delete "(e.g., steatosis, cholestasis, necrosis)";

Column 15, line 20, after "toxicity", insert --(e.g., steatosis, cholestasis, necrosis)--.

Column 15, line 25, delete "Liver toxicity biomarkers in urine";

Column 16, line 3, delete "Liver toxicity biomarkers in urine";

Column 19, line 46, delete "Liver Tox markers measured in Liver";

Column 20, line 3, delete "Liver Tox markers measured in Liver";

Column 22, line 16, replace "Table:" with --Table--;

Column 25, line 30, replace "Table:" with --Table--;

Column 25, line 49, replace "Table:" with --Table--; and

Column 26, line 53, replace "Table:" with --Table--.

Signed and Sealed this
Twenty-second Day of July, 2014

Michelle K. Lee
*Deputy Director of the United States Patent and Trademark Office*